United States Patent [19]

Takada

[11] Patent Number: 5,637,319
[45] Date of Patent: Jun. 10, 1997

[54] CONTROLLED-RELEASE PREPARATIONS

[76] Inventor: Kanji Takada, 618-2 Gokomachidori Gojoagaru Azuchi-cho,, Shimogyo-ku, Kyoto-shi, Kyoto-fu, Japan

[21] Appl. No.: 396,715

[22] Filed: Mar. 1, 1995

[51] Int. Cl.$^6$ .................................................. A61K 9/48
[52] U.S. Cl. .......................... 424/463; 424/451; 424/456; 514/962
[58] Field of Search .................................... 424/451, 455, 424/457, 463, 464, 474, 480, 452, 456; 514/962

[56] References Cited

U.S. PATENT DOCUMENTS

| | | | |
|---|---|---|---|
| 4,496,553 | 1/1985 | Halskov | 514/166 |
| 4,816,264 | 3/1989 | Phillips et al. | 424/468 |
| 4,980,173 | 12/1990 | Halskov . | |
| 5,217,720 | 6/1993 | Sekigawa et al. | 424/480 |
| 5,273,760 | 12/1993 | Oshlack et al. | 424/480 |
| 5,283,064 | 2/1994 | Suzuki et al. | 424/451 |
| 5,424,289 | 6/1995 | Yang et al. | 514/12 |
| 5,541,170 | 7/1996 | Rhodes et al. | 514/166 |
| 5,541,171 | 7/1996 | Rhodes et al. | 514/166 |

FOREIGN PATENT DOCUMENTS

| | | |
|---|---|---|
| 1172570 | 8/1984 | Canada . |
| 1017674 | 1/1966 | United Kingdom . |

OTHER PUBLICATIONS

Christensen, L.A., et al, Aliment. Pharmacol. Therap. 4, 523–533 (1990).
Dew, M.J., et al, Br. J. Clin. Pharmac., 14, 405–408 (1982).
Laursen, L.S., et al, Gvt 31, 1271–1276 (1990).
Lehman, K., Manufacturing Chemist & Aerosol News, pp. 39–41 Jun. 1973.
Stolk, L.M.L., et al, Pharmaceuti. Sch. Weekblad Scientific edition, 12(5), 200–204 (1990).
Rohm Pharma Brochure titled "Eudragit®" Lacquers for Tablet Coating, pp. 1–29, 1973.
Rohm Pharma Brochure titled "Eudragit™ L and S", pp. 3–4, 1973.
Niwa, K., et al, "Colon Delivery Technics for Oral Administration of Recombinant protein drugs (1), Development of Time Controlled–Release Colon Delivery System", The 114 Annual Meeting of Japan Pharmaceutical Society, Abstracts, 98, Mar. 5, 1994.
Takada, K., et al, "Colon Delivery Technics, Time Controlled–Release Colon Delivery Capsules" (Abstract), Drugs Delivery System, vol. 9, No. 4, 272, Jul. 10, 1994.
Takaya, T., et al, "Usefulness of Colon Delivery System for Oral Administration of Recombinant Protein Drugs" (Abstract), The Seventh Japanese–American Conference on Pharmacokinetics and Biopharmaceutics, Hiroshima, Japan, Jul. 31–Aug. 2, 1994.
Takaya, T., et al, "Colon Delivery Technics for Oral Administration of Recombinant protein drugs (2), Assessment of Oral rhG–CSF Preparation Using Colon Delivery System in Beagle Dogs", The 114th Annual Meeting of Japan Pharmaceutical Society, Abstracts, 98, Mar. 5, 1994.

(List continued on next page.)

Primary Examiner—John C. Bleutge
Assistant Examiner—Robert H. Harrison

[57] ABSTRACT

The invention provides oral controlled-release preparations suitable to deliver drugs to different sites of gastrointestinal tract and suitable to control the release rate of drugs. As a first function, targeting of drugs to the lower part of the small intestine or colon is possible with two technologies. One is a time-controlled release system comprising adjusting the balance of the tolerability and thickness of a water-insoluble material membrane and the amount of a swellable substance. The other one is an intestinal pressure controlled-release system comprising adjusting the thickness of a water-insoluble material membrane. As a second function, by adjusting pore number, pore size and the amount of gel-forming substance, a sustained-release preparation of extremely water-soluble, hydrophilic, low-molecular weight drug is possible.

1 Claim, 22 Drawing Sheets

OTHER PUBLICATIONS

Takaya, T., et al, "Colon Delivery Technics, Colon Delivery Capsules Using Gastrointestinal Pressure" (Abstract), Drugs Delivery System, vol. 9, No. 4, 273, Jul. 10, 1994.

Takada, K., et al, "Systematic Availability of 5–ASA after Oral Administration to Beagle Dogs with Colon Delivery Capsule" (Abstract), International Symposium on Recent Advances in Inflammatory Bowel Disease, Nara, Japan, Nov. 23–24, 1994.

(□) ; 20, (○) ; 30, (△) ; 60
Each point represents the mean SE ± of 3 experiments.

(□) : 20, (○) : 30, (△) : 60
Each point represents the mean ± SE of 3 experiments.

(□) ; 20, (○) ; 30, (△) ;60
Each point represents the mean ± SE of 3 experiments.

(□) ; 25 mg, (○) ; 50 mg, (△) ; 100 mg
Each point represents the mean ± SE of 3 experiments.

(□) ; 25 mg, (○) ; 50 mg, (△) ; 100 mg
Each point represents the mean ± SE of 3 experiments.

(□) ; 25 mg, (○) ; 50 mg, (△) ; 100 mg
Each point represents the mean ± SE of 3 experiments.

Each point represents the mean ± SE of 3 experiments.

(□) : 20, (○) : 30
Each point represents the mean ± SE of 3 experiments.

(□) : 25 mg, (○) ; 15 mg
Each point represents the mean ± SE of 3experiments.

□ actual example #4
○ actual example #5

(□) : control (placebo capsules)
(○) : EC capsules containing fluorescein and rhG-CSF, 30mg and 250 μg/10kg of body weight ※ : These capsules did not disintegrate in the gastrointestinal tract.

CONTROLLED-RELEASE PREPARATIONS

FIELD OF THE INVENTION

The present invention relates to oral controlled-release preparations for the administration of drugs to the gastrointestinal (GI) tract. More particularly, firstly, it relates to an oral time controlled-release preparation comprising a water-insoluble material, a drug and a swellable substance which is swollen with water to have the drug timely released. Secondly, it relates to an oral intestinal pressure controlled-release preparation comprising a drug and a water-insoluble material, which selectively releases a drug to its target site by controlling a thickness of the water-insoluble material membrane. Thirdly, it relates to an oral sustained-release preparation comprising a water-insoluble material, a water-soluble drug having a low molecular weight and a gel-forming material, from which a drug is slowly and sustainably released by controlling the kind and the amount of the gel-forming material inside formulated and a pore number on the water-insoluble material membrane.

BACKGROUND OF THE INVENTION

It has been difficult to administer protein/peptide substances orally because of their low bioavailabilities (BA) due to the extensive degradation both in the stomach and in the small intestine by digestive enzymes and hydrochloric acid. On the other hand, large intestine has been drawn less attention as absorption sites for drugs because large intestine was considered not to contain transport system for nutrient. Recently, it has been demonstrated that physiologically active polypeptide hormones are absorbed at large intestine, and so, large intestine have drawn attention as an absorption site for protein/peptide drugs. The following conventional drug delivery techniques have been used to deliver drugs to the lower intestines including lower part of small intestine, large intestine, colon and etc.; 1) colon specific polymer-coated preparations that are soluble in large intestines (for example, Science vol. 233: 1081–1084, 1986 and KAGAKU KOGYO 1991, october, p 55–63), and 2) drug release-controlling systems, taking advantages of osmotic pressure, so called "TES" (Time-controlled Explosion System that contains drug layer, swellable layer and water-insoluble polymer membranes) preparations (see, for example, Japanese patent publication KOKAI No. 62-30709 and Pharm. Tech. Japan vol. 7: 711–718, 1991), and 3) time-controlled drug release capsule such as Pulsincap® system using a swellable polymer stopper (see, for example, WO90/09168, 1990) and so forth have been known.

Also, drugs for the treatment of the inflammatory bowel disease (IBD) such as 5-aminosalicylic acid (5ASA) is used as a pro-drug, sulfasalazine that is an azo compound of 5ASA with sulfapyridine, because of extensive absorption of 5ASA during passage through the small intestine. As the target site of 5ASA is large intestine, to which an extremely small amount of 5ASA orally administered is delivered. Therefore, instead of 5ASA, its pro-drug sulfasalazine has been used clinically. However, side effects due to the hydrolyzed product, sulfapyridine, are now in great clinical problem.

Furthermore, it has also been difficult to administer anti-cancer drugs orally, because of the necrosis of the GI tract due to the exposure to high concentration of the anti-cancer drug molecules dissolved in the GI tract. Conventional oral slow-release tablets can control the release profile of anti-cancer drugs. However, these tablets contact directly to the mucosal surface of the GI tract. Therefore, the possibility of necrosis is high.

Since colon specific polymers and a polymer used in Pulsincap are new polymer, only insufficient data regarding their safeties are available. Additionally, time-controlled release system like TES, using osmotic pressure, a large amount of drug are required per batch because drug is coated onto the Nonpareils® (granule of sucrose; Freund Co., Ltd.) seeds with a spraying binder (e.g. hydroxypropylmethylcellulose etc.) in centrifugal granulator or blown up by air in fluid bed granulator. Therefore, these systems may not be practical if the drugs are expensive. In addition, in the case of pro-drug, especially new pro-drug compounds, data concerning their safeties are necessary for developing as therapeutic drugs.

As the result of an extensive study to overcome the above drawbacks and problems in conventional slow-release tablets, it has now been discovered preparations of the present invention which prevents the direct contact of drug molecules in the preparations to mucosal surface of the GI tract.

SUMMARY OF THE INVENTION

The first aspect of the present invention is an oral time controlled-release preparation for the targeting of drugs to gastrointestinal tract characterized by that a drug and a swellable substance are contained in a space surrounded by water-insoluble material membrane, said drug is omnipresent in the space, and said water-insoluble material membrane is permeable to water, or when said water-insoluble material membrane is not permeable to water, said water-insoluble material membrane on the side facing said swellable substance has one or more small pores to provide water for said swellable substance.

The preparation is designed to deliver a drug to a target site in gastrointestinal tract, particularly, the lower part of small intestine, large intestine and colon, more particularly, by controlling the release time of the drug from the preparation due to the disintegration lag-time which depends on a swellable pharmaceutical additives in the preparation.

The mechanism by which drug is released from this time-controlled release preparation is as follows: At first, the swellable substance swells with water that permeates through the micropores opened at the bottom of the water-insoluble polymer, ethylcellulose, made capsule from the outside. The inner pressure is caused by the swellable substance, which pushes the drug container that includes a drug and has been introduced into the capsule body. Then, the disintegration of the capsule occurs with the breakdown of the capsule cap by the drug container. However, it takes some time, lag-time, for drug to be released from the capsule. By adjusting the length of this lag-time, for example, colon delivery capsules can be developed.

In the present investigation, several factors that affect the drug release lag-time from the capsule have been studied. A good correlation has been obtained between the in vitro drug release characteristics from these capsules and the plasma drug concentration vs. time profiles after oral administration of the capsules to beagle dogs.

The second aspect of the present invention is an oral intestinal pressure controlled-release preparation for targeting to gastrointestinal tract characterized by that a drug is contained in a space surrounded by water-insoluble material membrane, and said drug is selectively released to a target site by controlling a thickness of said water-insoluble material membrane.

A preparation, such as an ethylcellulose (EC) made capsule, does not receive a high pressure on its surface just after oral administration by the peristalsis of gastrointestinal tract, because the contents in both gut and small intestine have high mobility. However, much water is absorbed from the large intestine and stool is formed there. Therefore, the mobility of the EC capsule is prevented by the stool formed there and the capsule cannot escape the pressure caused by the peristalsis. When EC capsule is disintegrated by the inner pressure of the large intestine, drug solution or drug suspension contained in the capsule is released. By using these inner pressure of large intestine derived from the peristalsis, EC capsule is designed as a device of colon delivery of drugs.

In the study of the invention, physicochemical properties of novel water-insoluble capsules made of EC is at first studied. In addition, the relationship between the thickness of an EC capsule and in vivo disintegration time has been studied using beagle dogs. Furthermore, using two representative drugs, namely, recombinant human granulocyte colony-stimulating factor (G-CSF) and 5-aminosalicylic acid as models of both recombinant protein drugs and drugs for inflammatory bowel disease, colon delivery capsules have been prepared and the availabilities of these preparations have been evaluated precisely.

The third aspect of the present invention is an oral sustained-release preparation for the administration of drugs to gastrointestinal tract characterized by that a drug which is water-soluble and has a low molecular weight, and a gel-forming material are contained in a space surrounded by water-insoluble material membrane, and said drug is continuously released during its passage through the gastrointestinal tract by controlling the kind and amount of said gel-forming material and pore number on said water-insoluble material membrane.

The conventional sustained-release preparations were designed by the following concepts: (1) the preparation is degraded partly for long period, (2) drug molecules are slowly released from the preparation through the limited area though with high concentration and (3) the preparation is composed of two portions that are a fast-release portion and a delayed-release portion. In either case, after the oral administration of such a sustained-release preparation, the gastrointestinal cells are exposed to high concentration of drug molecules. Especially, in the case of oral anti-cancer drug, patients often suffer from the necrosis of the gut or intestine. Therefore, an oral sustained-release strong anti-cancer drug preparation has not been developed yet.

The preparation of the present invention makes the release of drug molecules not through the limited area but through wide area of the preparation during a long period. Therefore, different from the conventional sustained-release preparations, the surrounding environmental concentration of drug molecules just after released from the preparation is low. The preparation is more properly applicable to drugs of which high concentration induces the serious side effect such as necrosis to the gastrointestinal tract.

According to the invention, especially, in the case of the drugs that are not suitable for being delivered and being released instantaneously to the upper parts on the GI tract, they are preferable to be delivered to the lower part of the small intestine and/or colon, or they are released at a constant rate in the GI tract.

For the constant rate release of drug, the release rate of drug molecule is regulated by the kind of the gel-forming material and the size and number of micropores opened on water-insoluble polymer membrane.

The preparation of the present invention allows (1) the delivery of protein/peptide drugs and drugs for the treatment of IBD etc. to the lower GI tract by releasing them to lower part of the intestine like lower parts of small intestine, colon and so forth, (2) the release of drugs such as anti-cancer drug, anti-inflammatory drug and anti-asthmatic drugs etc. at a constant rate during its passage through the GI tract and (3) sustained-release profiles by combining a fast-release tablet or capsule and a delayed-release tablet or capsule.

All polymers used in this invention have been approved for use as pharmaceutical additives and are highly safe. Additionally, even if the drug is expensive, the drug can be filled in the preparation after manufacturing it as solid dispersion or as a mini-tablet containing a required quantity. Therefore, loss of the drug during the manufacturing process can be extremely small.

Since the preparations of the present invention are build up with a water-insoluble polymer, it can stand even when the preparations are filled with propylene glycol (PG) which are a good solvent for highly hydrophobic drugs. Although PG is useful for increasing the bioavailability of highly hydrophobic drugs, no capsule has been manufactured so far that is resistant to PG.

DETAILED DESCRIPTION OF THE INVENTION

Figure 1A:
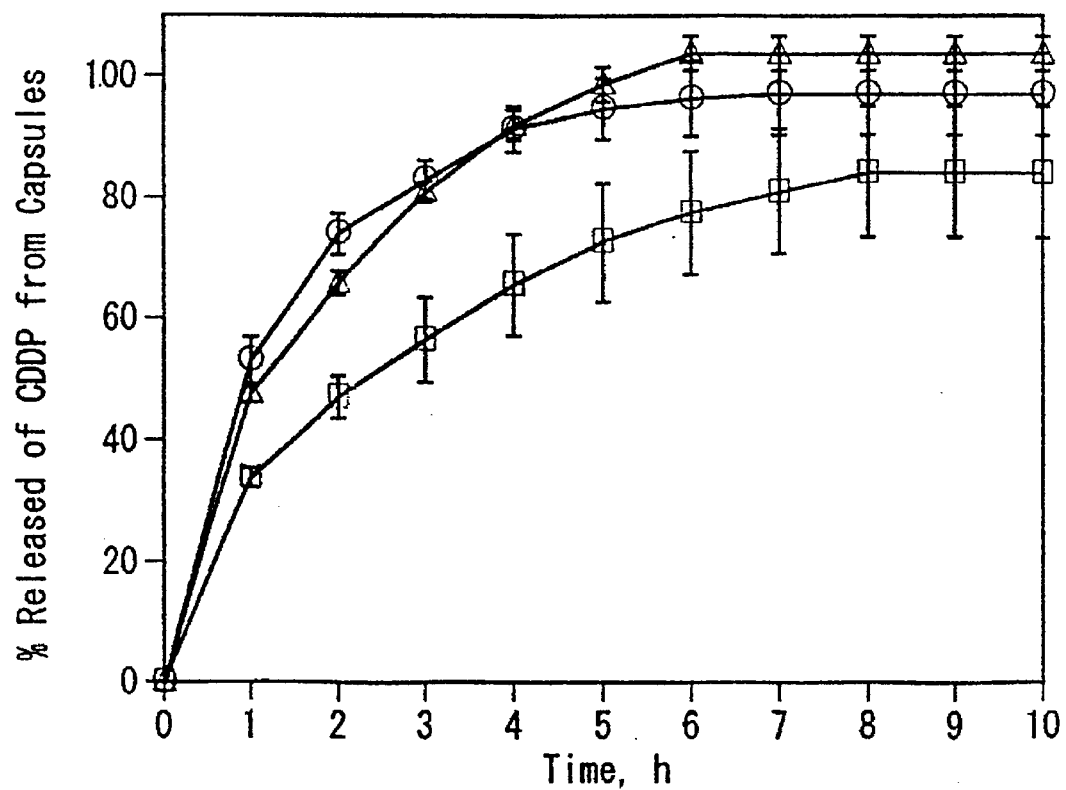
FIG. 1a. Dissolution profiles of cisplatin (CDDP) from capsules with different numbers of micropore (Amount of carbopol is 25 mg).
Figure 1B:
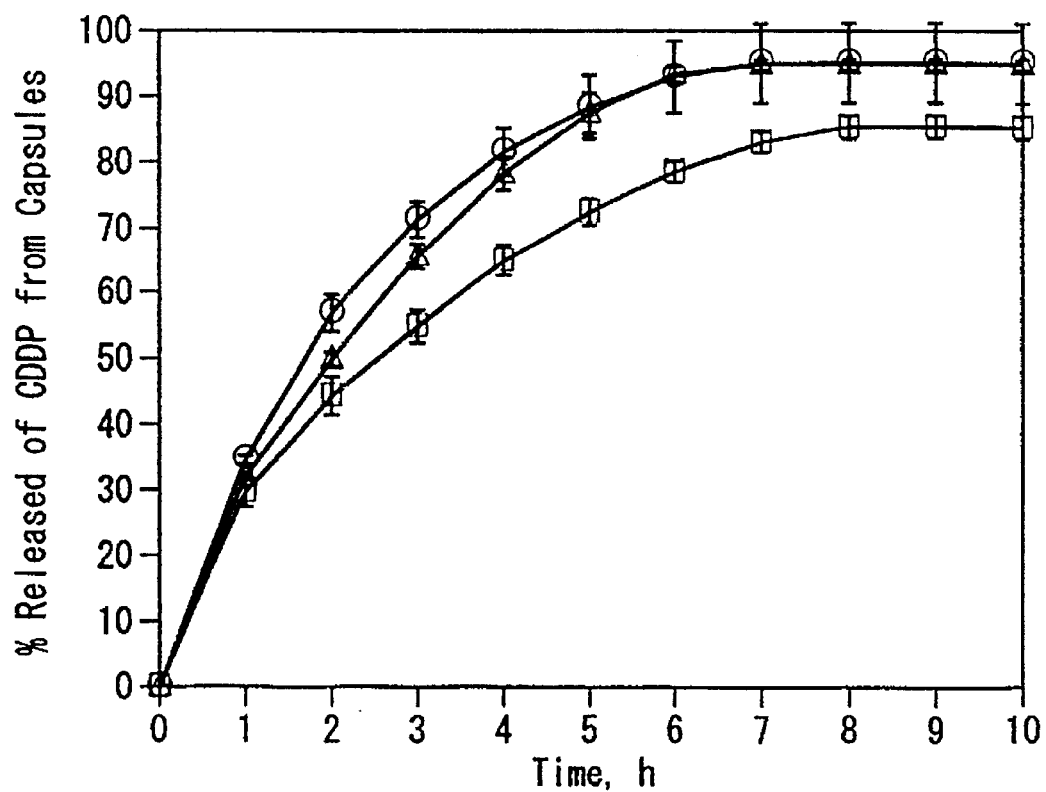
FIG. 1b. Dissolution profiles of CDDP from capsules with different numbers of pore (Amount of carbopol is 50 mg).
Figure 1C:
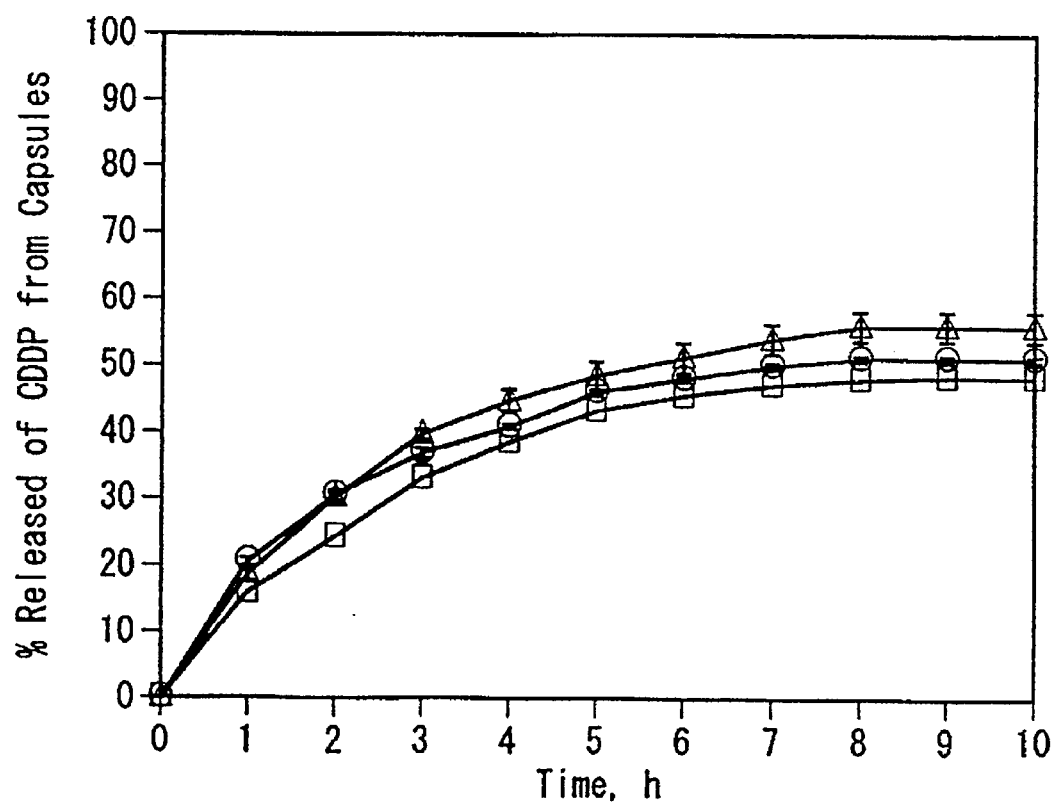
FIG. 1c. Dissolution profiles of CDDP from capsules with different numbers of pore (Amount of carbopol is 100 mg).

The volume of the space surrounded by a water-insoluble material is usually within the size available for oral administration. Therefore, the preparations of the present invention are capsules or tablets.

Any drug capable of administering orally can be used as a drug in the controlled-release preparations of the present invention. The oral controlled-release preparations are particularly designed for a group of drugs that are not suitable for releasing instantaneously in the upper part of the GI tract. This includes (1) therapeutic agents for IBD (for example, 5-aminosalicylic acid and methylprednisolone etc.), (2) anti-cancer agents (for example 5-fluorouracil etc.) that are effective for the treatment of colon carcinoma, (3) protein/peptide or peptide-like drugs such as insulin, calcitonin, human granulocyte colony-stimulating factor, erythropoietin, interferon and various interleukins and so forth.

When a drug is contained in the space as solution or suspension, the uniformity of the preparation is acceptable.

A solid dispersion composition is prepared by dispersing a drug into water-soluble materials such as macrogel (polyethylene glycol; PEG) derivatives (e.g. PEG 1500, i.e., polyethylene glycol having a molecular weight of 1500, PEG 1000, i.e., polyethylene glycol having a molecular weight of 1000 etc.) and the mixture of citric acid, tartaric acid and HCO-60® (Nikko Chemicals Co., Ltd.) (polyoxyethylated, 60 μmol, hydrogenated castor oil having a Saponification Value of 43–51 and a Hydroxyl Value of 40–48) etc.

The amount of the drug in unit-dosage formulations can be adjusted as desired.

As a water-insoluble material, ethylcellulose (EC) (Shin-etsu Chemical Industry Co., Ltd.), polyvinyl acetate, aminoalkyl methacrylate copolymer particularly copolymer of acrylic and methacrylic acid esters having methyl and ethyl ester groups and containing quaternary ammonium groups present as chloride salts (Eudragit® RS; Rohm Pharma Co., Ltd.), chitin, chitosan, wax-type coating materials, hardened oil and so forth can be used in the invention. As these water-insoluble materials show a variety of physical properties (permeability and strength) depending on the extent of cross-linking etc., compounds with suitable physical properties can be selected to the desired releasing profiles.

Moreover, as plasticizer, dibutyl sebacate or triethyl citrate can be mixed.

The water-insoluble material in unit-dosage formulations is 1–50% by weight, preferably, 2–40%, or more preferably, 3–30%. The shape of the water-insoluble materials is not restricted, but usually, they have a film-like shape.

L-HPC (low-substituted hydroxypropyl cellulose), sodium starch glucolate (Explotab®; Edward Mendell Co., Ltd.) and so forth have been used as swellable substances in the invention. Additionally, extent of swelling can be regulated by mixing stearic acid and so forth as necessary. Although the size of the pore of the water-insoluble polymer membrane can control the release rate of drug, gel-forming polymer such as carboxyvinyl polymer (Carbopol® 934P; BF Goodrich Co., Ltd.) etc. can be formulated into the preparation to more retain the release rate of drug molecules.

A swellable substance in unit-dosage formulation is 1–60% by weight, preferably, 2–50%, or more preferably, 5–30%.

The pore size of the time controlled-release preparation should be 10–1000 μm in diameter, preferably, 50–900 μm, or more preferably, 100–800 μm so that water can pass through with ease.

The water-insoluble materials that are used to prepare the time-controlled release system described above can be also applicable to the intestinal pressure controlled-release system.

A thickness of the intestinal pressure controlled-release system which depends on the physico-chemical properties of the water-insoluble polymer, is about from 30 μm to about 70 μm, preferably, about 35–60 μm.

The target site of the intestinal pressure controlled-release preparation is the large intestine or colon, preferably, colon.

The water-insoluble materials that are used to prepare the time-controlled release system described above can be also applicable to the sustained-release preparations.

As a gel-forming materials used in the sustained-release preparation, there can be mentioned the following substance; carboxyvinyl polymer, sodium alginate, sodium carmellose, calcium calmellose, sodium carboxymethyl starch, polyvinyl alcohol, hydroxypropylcellulose, hydroxyethylcellulose, methylcellulose, more preferably, carboxyvinyl polymer.

The number of the micropores on the water-insoluble materials is, though depending on pore size, from about 10 to about 100. In the case of a #00 capsule, the pore size is fixed to 800 μm. However, the pore number of about 30—about 60 is more preferable.

The amount of gel-forming material used for the preparation of sustained-release preparations is about from 1 w/w % to about 30 w/w %, and more preferably from about 1.5% to about 20%. The formulated amount of drug is not restricted and is from about 1% to 60%, more preferably from 2% to 50%. The pore size is from about 50 μm to about 1000 μm in diameter, more preferably from 100 μm to 800 μm.

The sustained-release preparation is especially suitable for preparing oral long-acting preparation of hydrophilic, water soluble, low-molecular weight drug and as the preparation is surrounded by water-insoluble polymer membrane, the direct contact of a drug molecule in the preparation onto the surface of the GI cells is prevented. Therefore, according to the sustained-release preparation of the present invention, the drug may include, for example, ant-cancer drugs (cisplatin, carboplatin etc.) and so forth.

Figure 2A:
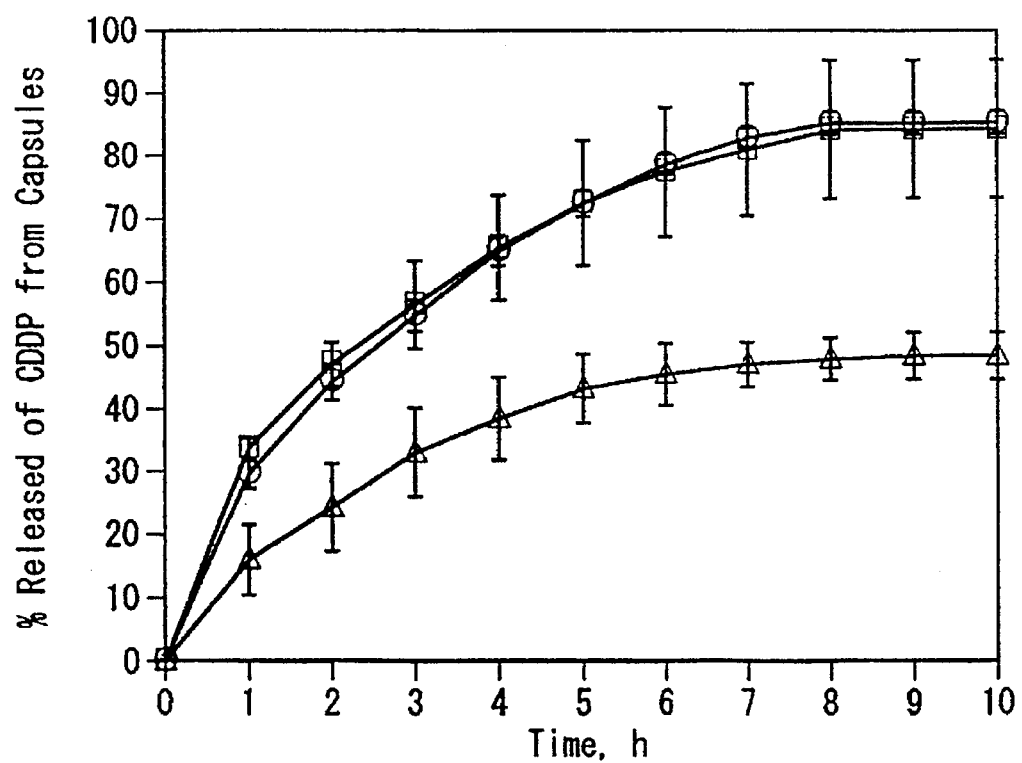
FIG. 2a. Dissolution profiles of CDDP from capsules containing different amounts of carbopol (Pore number is 20).
Figure 2B:
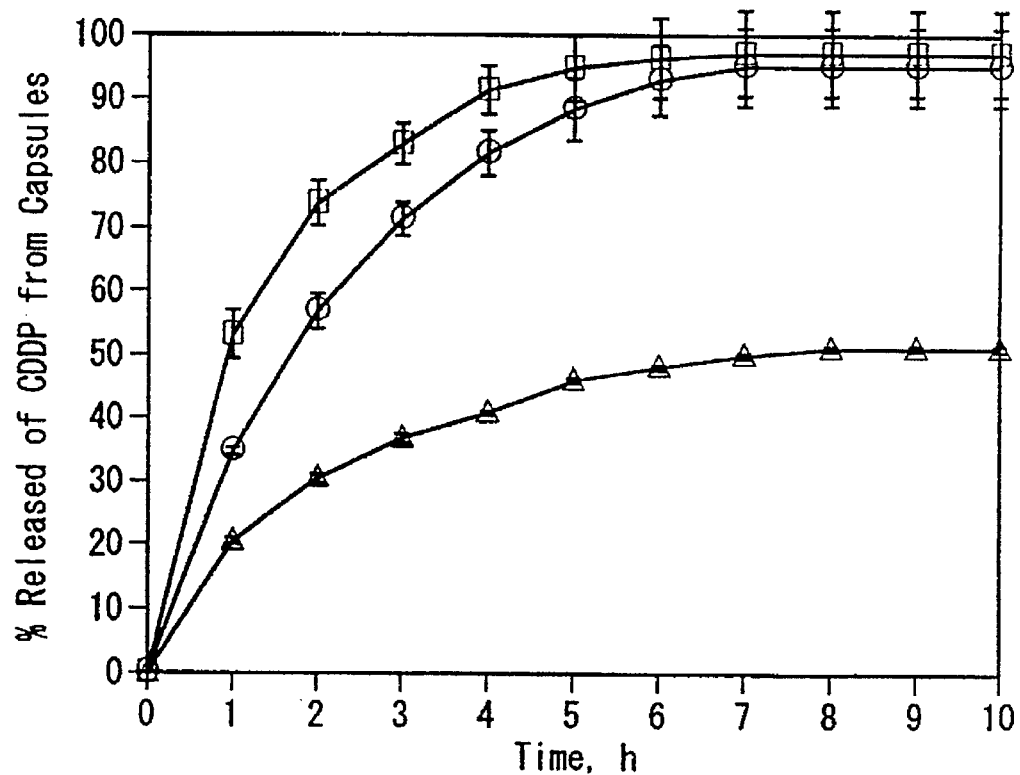
FIG. 2b. Dissolution profiles of CDDP from capsules containing different amounts of carbopol (Pore number is 30).
Figure 2C:
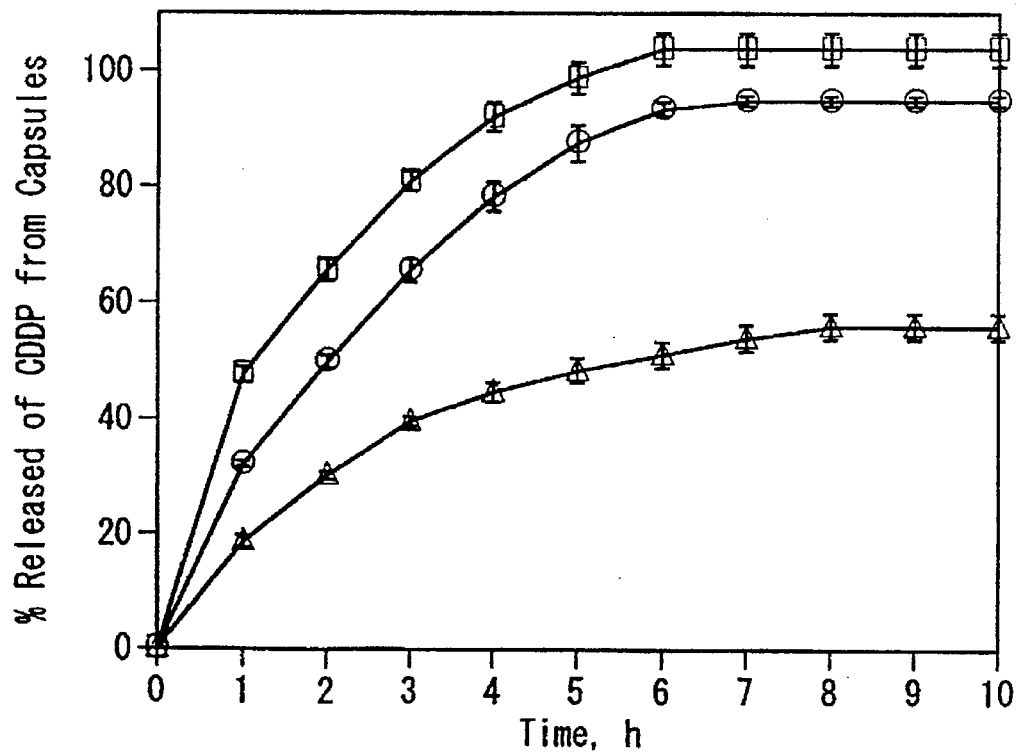
FIG. 2c. Dissolution profiles of CDDP from capsules containing different amounts of carbopol (Pore number is 60).

According to the experiment concerning the effects of pore number and the amount of formulated gel-forming polymer on the release rate of the formulated drug, the following results have been obtained;

The release rate of extremely hydrophilic low-molecular weight drug such as cisplatin from the sustained-release preparation is affected by the following three factors; (1) pore number made on the water-insoluble polymer, (2) pore size and (3) amount of gel-forming material inside the preparation. From the standpoint of mechanical operation of opening many uniform pores, the pore size was fixed to be 800 μm. Under the fixed pore size condition, the effects of the pore number was at first examined and the release patterns of cisplatin from the preparations are shown in FIGS. 1a, b and c. As the pore number increases from 20 to 30, the release rate of cisplatin increases when the amount of gel-forming polymer was 25 mg and 50 mg. However, prolonged effect was not observed by increasing the pore number from 30 to 60. In addition, when the amount of gel-forming polymer was increased to 100 mg, the pore number did not affect the release rate of cisplatin any more. The release study data are summarized with respect to the effect of the amount of gel-forming polymer and the results are shown in FIGS. 2a, b and c. When pore number is 30 and 60, as the amount of gel-forming polymer increases from 25 mg to 50 mg, the release rate of cisplatin decreases. However, when pore number is 20, the effect of the increase of the amount of gel-forming polymer did not appear.

Figure 3:
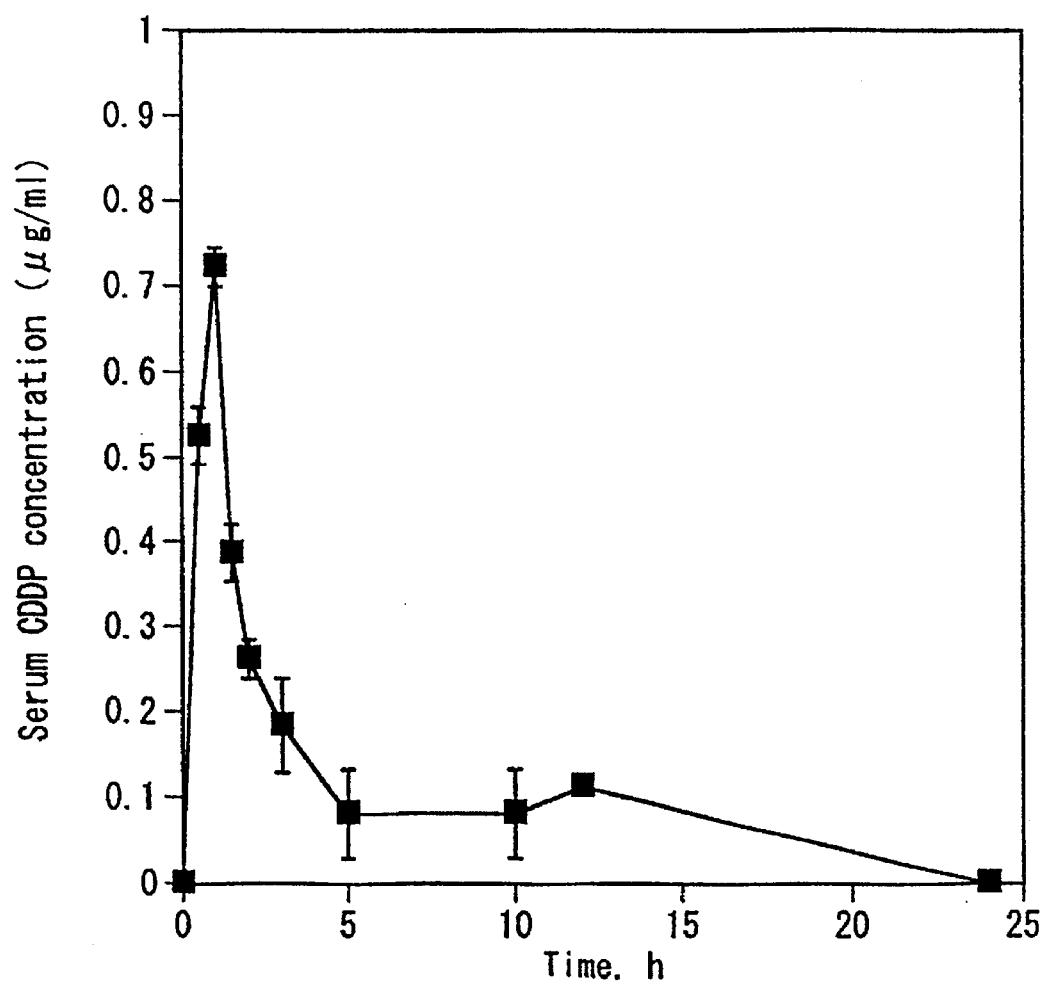
FIG. 3. Serum CDDP concentration vs. time curve after oral administration of CDDP solution to rabbits, 20 mg/head.

The effects of the pore number and the amount of gel-forming polymer on the release profiles of cisplatin was confirmed in the in vivo study after oral administration of the preparations to rabbits using a reference preparation, cisplatin solution, at 20 mg/kg. FIG. 3 shows the serum cisplatin concentration-time curve after oral administration of cisplatin solution. The absorption rate of cisplatin is so rapid that the serum peak level appears within 1 hr. However, thereafter, serum cisplatin level declined rapidly.

Figure 4:
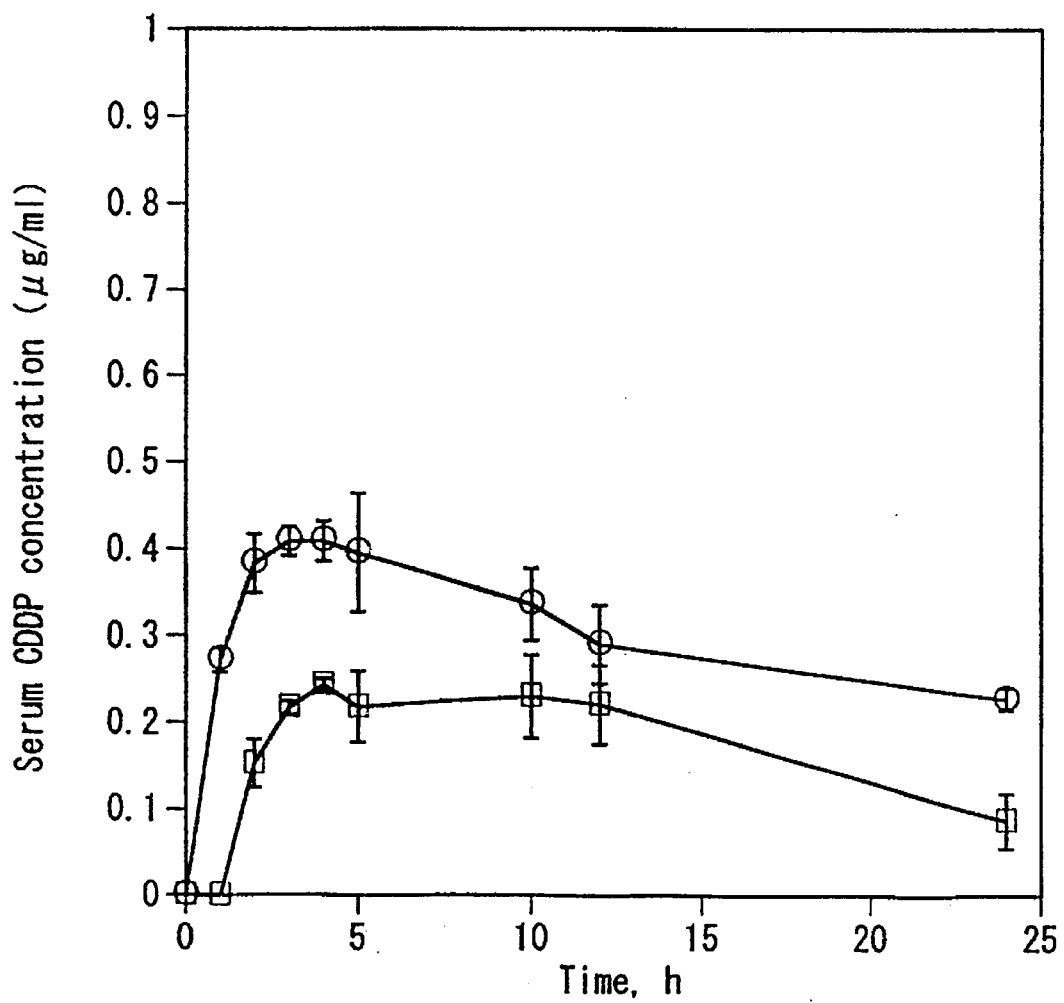
FIG. 4. Effects of pore number on Serum concentrations of CDDP after oral administration to rabbits, 20 mg/head (amount of carbopol is 25 mg).
Figure 5:
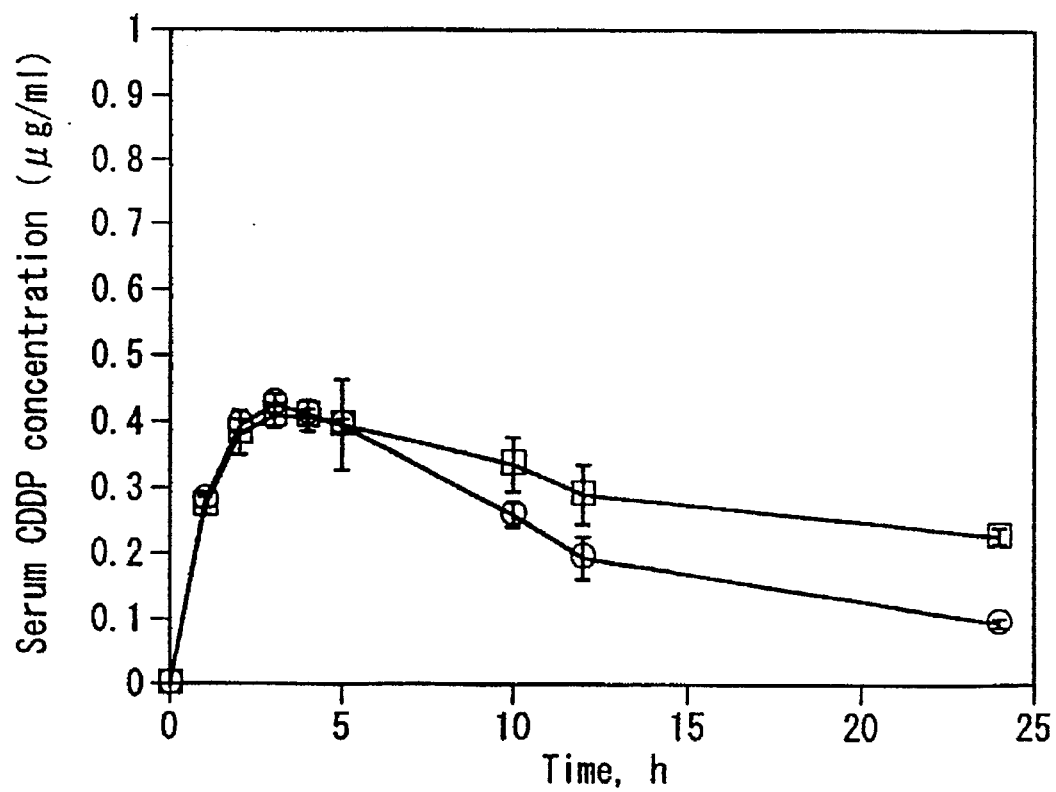
FIG. 5. Effects of amount of carbopol on serum concentrations of CDDP after oral administration to rabbits, 20 mg/head (pore number is 30).

FIGS. 4 and 5 show the serum cisplatin level vs. time curves after oral administration of the sustained-release preparation of the present invention. From FIG. 4, it is suggested that serum cisplatin levels significantly increases as the pore number increases from 20 to 30. However, as shown in FIG. 5, there is not a significant difference on serum cisplatin level vs. time curves between two groups, because the prescribed amount of gel-forming polymer was less than 25 mg.

Time-controlled drug delivery system in this invention can be prepared as follows.

For example, (A) in case of preparations coated with water-insoluble materials, if the water-insoluble material is ethylcellulose (EC), for example, (1) form EC capsule body (outer one) of 120 μm thickness by coating the inner or outer surface of a conventional gelatin capsule body and dissolving gelatin in warm water, (2) make micropores at the bottom of the EC capsule body, (3) insert a tablet of a swelling substance, low-substituted hydroxypropyl cellulose (L-HPC), that is made by direct compression, (4) a drug is dissolved in polyethylene glycol (PEG) 1000 under warming and is filled into another EC capsule body (inner one) that can be smoothly inserted to the outer one, (5) thereafter, capsule cap made of EC is attached to the EC capsule body by a concentrated EC solution, glue.

Then, (B) in the case of preparations containing a drug as a tablet, for example, (1) make a tablet with L-HPC alone or after mixing L-HPC and lactose or stearic acid with certain proportions (first-layer), (2) make a two-layer tablet after mixing the drug with crystalline cellulose and compress them on the first-layer, (3) perform coating with EC solution to the two-layer tablet and make micropores mechanically or by laser ray on the first layer of the tablet, (4) finally, sugar coating is performed.

The intestinal pressure-controlled preparation of the invention can be prepared, for example, as previously described as (A) (1) in which the thickness of outer or inner coating depends on the target site. Additionally, (C) if the drug is liquid or is used as solution or suspension, (1) coat the inner surface of a whole gelatin capsule with EC by introducing EC solution through a pore made at the top of gelatin capsule followed rotating the capsule at horizontal position and evaporating the solvent, (2) fill a drug solution dissolved in a solvent such as propylene glycol (PG) into the EC coated gelatin capsule through a pore at the top of the capsule, (3) close the pore by the drop of EC glue.

To prepare a sustained-release preparation of the present invention, for example, (1) make an EC capsule cap and a body having about 150 μm thickness, (2) make a predetermined number of micropores on both the capsule body and cap, (3) make a tablet from a mixture of drug and gel-forming material etc., (4) insert the tablet into the EC capsule body, (5) finally, the EC capsule cap is attached to the capsule body by EC glue.

EXAMPLE

Practical embodiments of the invention are illustratively shown in the following non-limiting Examples.

Example 1

Figure 6:
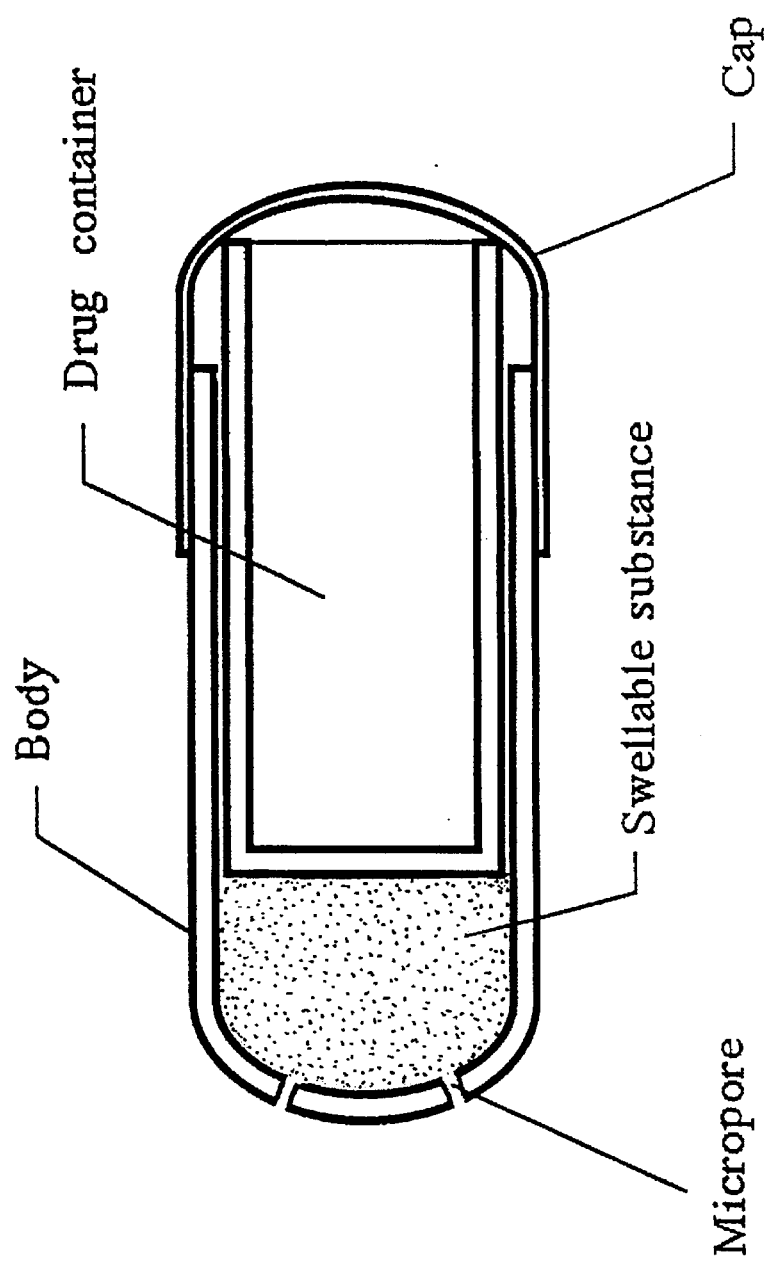
FIG. 6. A time controlled-release capsule prepared in Example 1.

The time-controlled release preparation for the delivery of drug to the lower part of the intestine is schematically shown in FIG. 6 and was prepared as follows. A capsule body and a drug container were made of 100G grade EC (Shin-etsu Chemical Industry Co., Ltd.). To make the capsule body, 1.2 g of 100G grade EC was dissolved in 16 ml of the mixture of methylene chloride and methanol (4:1) with stirring. To the body of #00 gelatin capsule, about 1 ml of the prepared EC solution was fulfilled. Thereafter, the solvent was evaporated overnight at 6° C. in a refrigerator. After the gelatin layer was dissolved in water at 37° C., EC capsule body was obtained. The thickness of the obtained EC capsule body was approximately 110 μm. At the bottom of the capsule body, four micropores of which size was 400 μm were mechanically made. The drug container was also made of EC which is inserted to the capsule body. To make an EC capsule cap, 10G grade EC solution, 25 mg/ml, were fulfilled to a #00 gelatin capsule cap. After the solvent, methylene chloride and methanol mixture, was evaporated, an EC coated gelatin cap was obtained. This cap was used without dissolving gelatin. The thickness of the EC cap was about 63 μm. After 60 mg of a swellable substance, L-HPC(LH-20), was put into the EC body, EC body was centrifuged for 4 min at 600 g. Furthermore, 60 mg of another swellable substance such as L-HPC(LH-21) was overlaid on L-HPC (LH-20) layer. To the drug container, 15 mg of 5-fluorouracil (5-FU) dissolved in 0.45 ml of the mixture of polyethylene glycol (PEG) 1500 and HCO-60 (Nikko Chemicals, polyoxyethylated, 60 μmol, castor oil derivative), (9:1) was introduced after mixing well. Thereafter, the drug container was inserted into the EC capsule body. The EC coated gelatin capsule cap was then attached to the EC body and were sealed by means of concentrated EC solution.

Example 2

The time-controlled release capsule as described in Example 1 is prepared except that the thickness of the EC coated capsule is different. To make an EC capsule cap, a 10G grade EC solution, 28 mg/ml, are fulfilled to the #00 gelatin capsule cap. After the solvent is evaporated, an EC coated gelatin cap of which thickness is about 75 μm is obtained. To 15 mg of 5-FU dissolved in PEG 1000 and HCO-60 is introduced into a container. By attaching the EC coated cap, the release time-controlled capsule is prepared as the same method in Example 1.

Example 3

An EC capsule body and an EC coated gelatin capsule cap are prepared as described in Example 2 except that a tablet containing the drug is substituted for the drug container. In this case, at first, a long tablet containing 30 mg of 5-FU of which size is two fold length as compared to the drug container in Example 1, is made by direct compression with 800 mg of crystalline cellulose. EC coating is performed (thickness; about 120 μm). This long tablet is cut to prepare two tablets. Thus obtained tablet can be used as a drug container. Thereafter, a release time-controlled capsule is prepared as the same method in Example 1.

Example 4

An intestinal pressure controlled-release capsule is prepared. Surface of a #00 gelatin capsule is coated by evaporating 3.0% 7G grade EC i.e., ethyl ether of cellulose having a viscosity of 5.6 cp. 80.0 to (Shin-etsu Chemical Industry) solution dissolved in a mixture of methylene chloride and methanol (4:1) at 6° C. in a refrigerator. The thickness of the EC coating is about 38 μm. The gelatin layer of the EC coated capsule body is removed by dissolving in water, the length is 4 mm from the open end. To the capsule body, 0.85 ml of PEG 1000 solution (at 40° C.) containing 125 mg of 5-aminosalicylic acid (5ASA) is introduced. After cooled well, EC coated capsule cap in which base, PEG 1000, is contained is attached to the body with the aid of concentrated EC solution.

Example 5

An intestinal pressure controlled-release capsule is prepared though the coating thickness was changed as compared to Example 4. The concentration of the used 7G grade EC solution is 3.5%. EC coating (thickness; about 48 μm) is performed as the same method as described in the previous example. In addition, 5ASA, 125 mg, is introduced into the capsule.

Example 6

An intestinal pressurecontrolled-release capsule is prepared as described in Example 5. The thickness of the 22G grade EC coating is about 48 μm. To prepare a drug solution, a solvent is at first prepared. That is, 50 mg of polyoxyethylated, 60 μmol, castor oil derivative, (HCO-60®; Nikko Chemicals) and 350 mg of anhydrous citric acid are dissolved in 0.8 ml of propylene glycol (PG). The 250 mg of lyophilized recombinant human granulocyte colony-stimulating factor (rhG-CSF) is dissolved in 0.8 ml of thus prepared PG solution and is introduced into the capsule. Thus, the preparation was made by sealing the pore with EC glue.

Example 7

Figure 7:
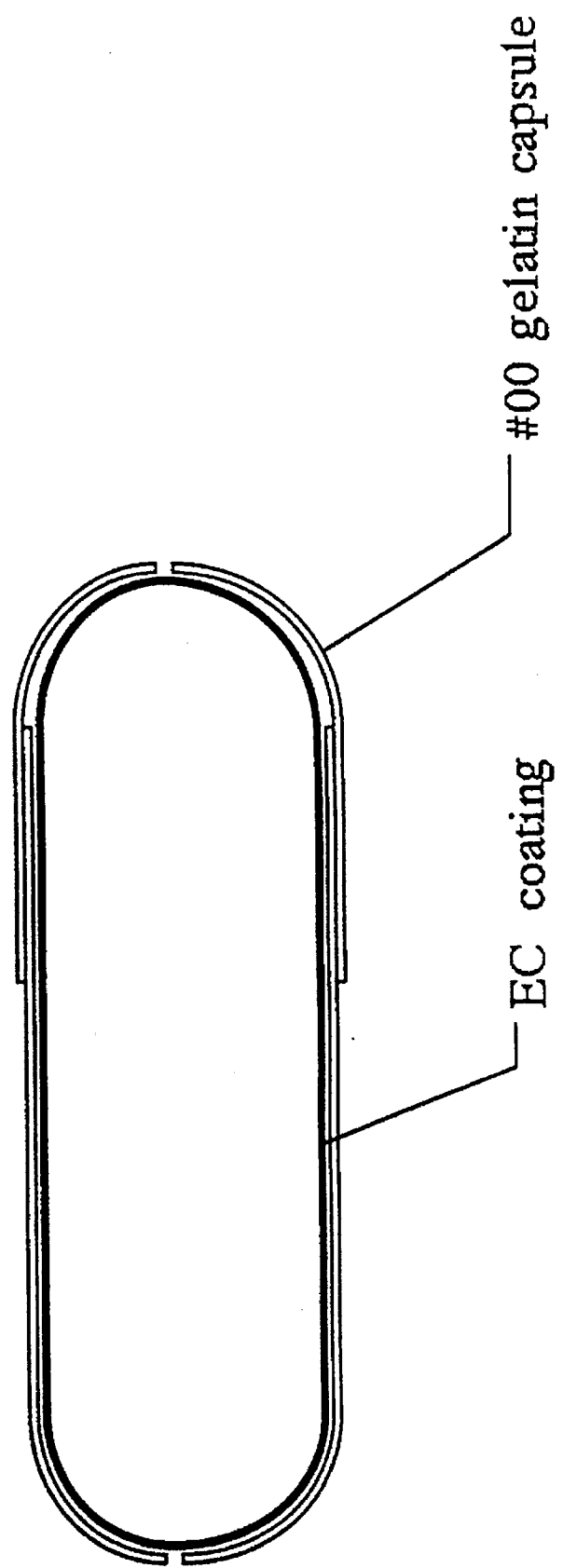
FIG. 7. An intestinal pressure-controlled release capsule (made of ethylcellulose) prepared in Example 7.

After pores (diameter: about 2 mm) are made at the top and the bottom of a #00 whole gelatin capsule, 250 μl of 18% EC (grade 7G) solution is introduced into the capsule and the inner surface of the capsule is coated with EC (thickness; about 43 μm) by rotating it horizontally at 40° C. for 12 h (FIG. 7). After the pore at the bottom is sealed with concentrated EC (grade 7G) solution, EC capsule is filled with 0.8 ml of PEG solution, mixture of PEG 1500 and PEG 4000 (4.5:1), at 40° C. containing 2000 unit of eel calcitonin through a pore on the top. The capsule is sealed with EC glue at room temperature.

Example 8

Figure 8:
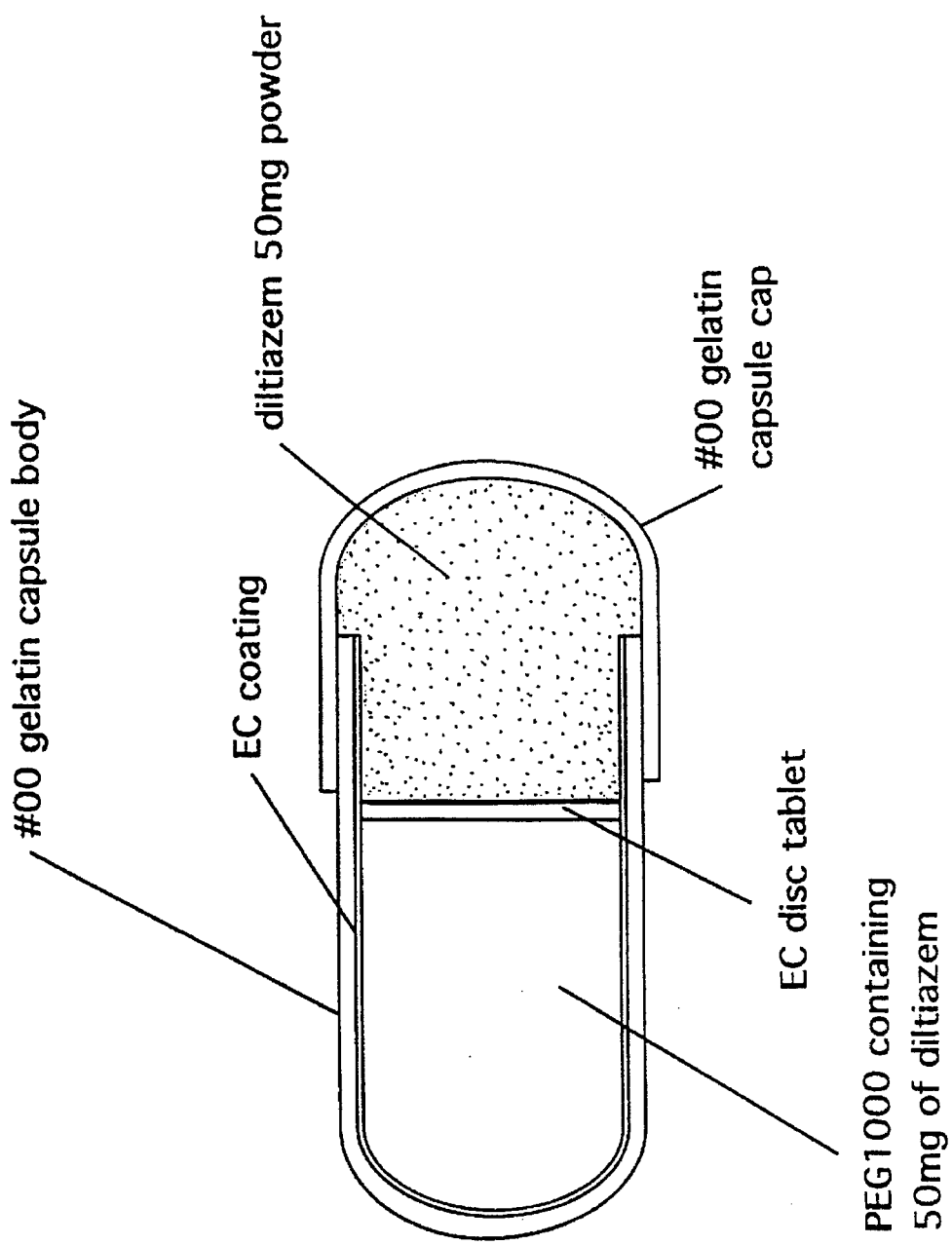
FIG. 8. A sustained-release capsule composed of two portions, i.e. fast-release and delayed-release portions in Example 8.

Capsule composing of both a short-release portion and a delayed-release portion (FIG. 8) is prepared as follows. An EC coated gelatin capsule body is prepared as described in Example 5. An 0.45 ml of PEG 1000 solution containing 50 mg of diltiazem hydrochloride is introduced into the body. After cooled well, a thin tablet made of EC of which size is 8 mm (o.d.)×2 mm thickness is attached inside the capsule body with the aid of EC glue. In addition, 50 mg of diltiazem hydrochloride powder is introduced into the body and a cap is attached to the body.

Example 9

Figure 9:
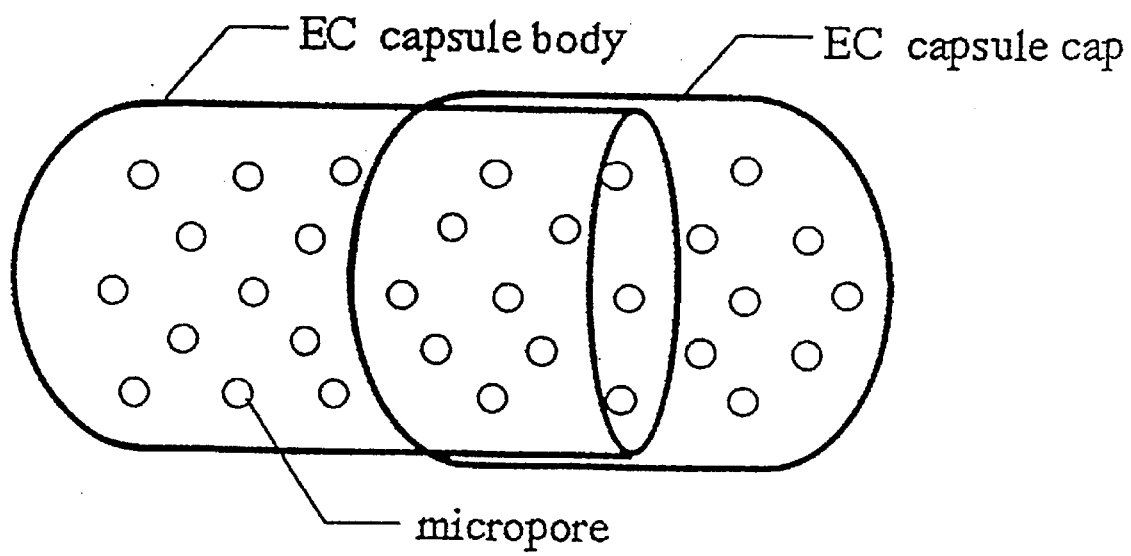
FIG. 9. A microporous EC capsule prepared in Example 9.

Sustained-release preparation is prepared as follows. An EC (grade 100G) capsule body and a cap (thickness; about 150 μm) are made by the method described as in Example 1 using a conventional #00 gelatin capsule. An EC capsule having 20 micropores (diameter; about 800 μm) are mechanically made at regular space (FIG. 9). A drug, 20 mg of cisplatin, 25 mg of Carbopol 934®, 450 mg of sucrose and 200 mg of Tween 80 are mixed well and the resultant mixture is inserted into the capsule body. Finally, capsule cap is attached to the body with EC glue.

Example 10

A sustained-release preparation was made as described in Example 9 except that the number of micropores is 30 in Example 10.

Example 11

A sustained-release reparation was made as described in Example 9 except that 50 mg of Carbopol 934® was used in Example 11.

In vitro drug release profile of the preparations of the present invention was studied according to a procedure of the paddle method defined in the Japanese Pharmacopeia XII.

Dissolution Test

Test preparations

The preparations according to Examples 1, 2, 3, 9, 10 and 11 were used for in vitro drug release experiments.

Test method

The test was performed according to the procedure of the paddle method (JPXII). A dissolution media employed were the 1st solution (JPXII, pH 1.2) and the 2nd solution (JPXII, pH 6.8). Nine hundred ml of the dissolution medium was used at 37°±0.1° C. at 100rpm. Test capsule was put into a stainless sinker. After being enclosed in the sinker, the capsule was put into 900 ml of the 1st solution maintained at 37° C. The shaft was then placed in the fluid at 37° C. and the paddle was rotated at 100 rpm. To simulate the transit from gastric to intestinal pH, samples of 1st solution were replaced one hour later with the 2nd solution. The release profile of 5-FU was estimated by measuring the appearance of the drug by HPLC method. The cisplatin concentration was estimated by analyzing for platinum by atomic absorption spectrophotometry.

Test result

Dissolution test data are shown in Table 1. The drug release is dependent on the thickness of EC coated cap in the cases of the time-controlled release systems, preparations 1, 2 and 3. In the case of preparations 9, 10 and 11, sustained-release profiles are observed.

TABLE 1

| Test Preparation | Dissolution rate (%) | | | | | | | | | | |
|---|---|---|---|---|---|---|---|---|---|---|---|
| | 0.5 h | 1 h | 1.5 h | 2 h | 3 h | 4 h | 5 h | 6 h | 7 h | 8 h | 24 h |
| 1 | 0 | 0 | 0 | 5 | 24 | 63 | 89 | 100 | 100 | 100 | 100 |
| 2 | 0 | 0 | 0 | 0 | 0 | 9 | 93 | 100 | 100 | 100 | 100 |
| 3 | 0 | 0 | 0 | 0 | 0 | 12 | 97 | 100 | 100 | 100 | 100 |
| 9 | 16 | 33 | 40 | 48 | 53 | 63 | 71 | 76 | 78 | 81 | 100 |
| 10 | 29 | 53 | 62 | 73 | 81 | 88 | 90 | 98 | 99 | 100 | 100 |
| 11 | 15 | 35 | 45 | 57 | 71 | 80 | 85 | 92 | 93 | 94 | 100 |

The bioavailability of the preparations according to the invention was studied using beagle dogs and rabbits.

Absorption Test in Experimental Animals

Test method

In case of preparations of which drug release mechanism is based on the intestinal pressure, drug release profiles of the preparations in Examples 4, 5, 6, 7 and 8 cannot be measured by in vitro release experiments. In addition, in the case of sustained-release preparations in Examples 9, 10 and 11, the long-acting efficiency must be confirmed in the in vivo animal study after oral administration. Therefore, in vivo pharmacokinetics study was performed using beagle dogs and rabbits. In the in vivo study, the preparations of the Examples except examples 6, 10 and 11 were administered to dogs and rabbits, respectively. Adult male beagle dogs and rabbits were fasted overnight for at least 12 h. At 30 min before drug administration, 1.0 ml of the blank blood sample was removed from the jugular vein and/or ear vein, respectively. After the oral administration of a test capsule containing 5ASA, 5-FU, eel calcitonin, diltiazem or cisplatin in 20 ml of water, 1.0 ml aliquot of blood samples were collected. The standard sampling schedule was at 0, 1, 2, 3, 4, 5, 6, 7, 8, 9, 10, 12 and 24 h. A standard solid meal of commercial food was given at 6 h after drug administration. No additional food was given during the study although free access to water was allowed. The plasma or serum was obtained by centrifuging the blood sample at 8000 g for 2 min. These plasma and serum samples were immediately frozen in a deep freezer at −20° C. until analyzed.

Plasma 5ASA and 5-FU concentrations were measured by an HPLC method after extraction of the drug from the plasma sample. The serum cisplatin level was determined by analyzing for platinum by atomic absorption spectrophotometry. The plasma calcitonin level was determined by an ELISA method.

Test results

Figure 10:
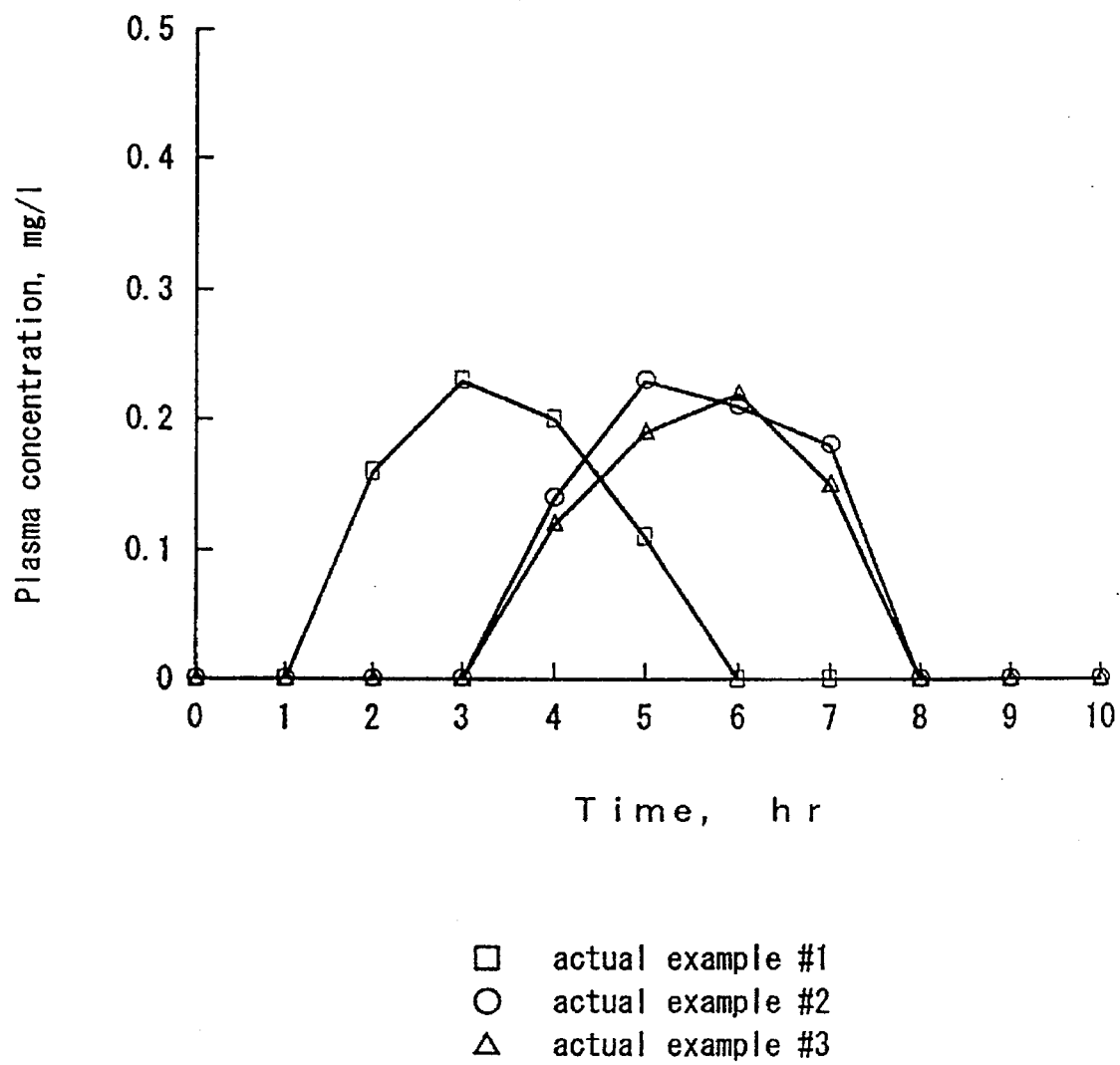
FIG. 10. Plasma 5-fluorouracil (5-FU) concentrations vs. time curves after oral administration of preparations in Example 1, 2 and 3 to male beagle dog.
Figure 11:
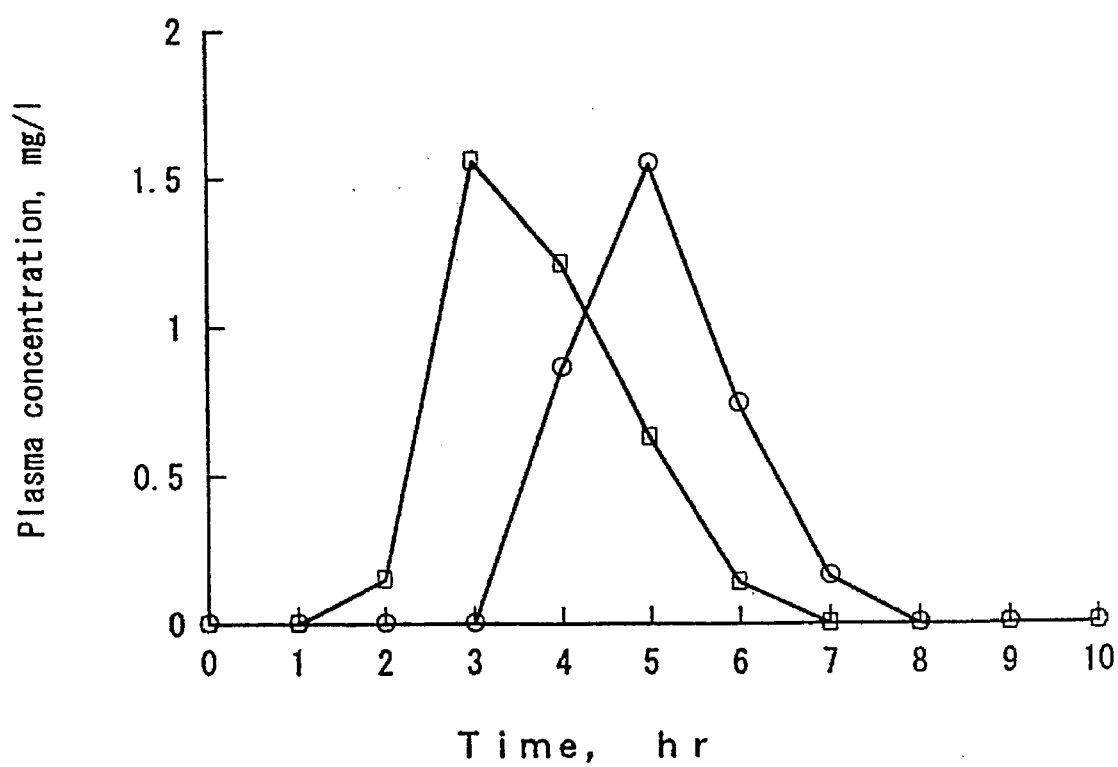
FIG. 11. Plasma 5-aminosalicylic acid (5ASA) concentrations vs. time curves after oral administration of preparations in Example 4 and 5 to male beagle dog.

FIG. 10 shows the plasma 5-FU level vs. time curve in the dog after oral administration of three kinds of capsules of each preparation of Example 1, 2 or 3 to individual dog where the dose of 5-FU is 45 mg/dog. The peak time, Tmax, when the plasma 5-FU level reaches to its maximum level is used as a parameter for estimating the release time of drug in the GI tract after oral administration. As the thickness increases from 63 μm to 75 μm, the Tmax increases. FIG. 11 also shows the plasma 5ASA concentrations vt. time curves after oral administrations of preparations of Examples 4 and 5, respectively. Tmax is dependent on the thickness of EC coating. According to the report of Anderson (1070), for the dog, gastric emptying is 3–5 h, small intestine transit time is about 1 h and colonic transit time is 10–12 hr. On the other hand, Mizuta et al. (1989) reported that the small intestinal transit time in beagle dog is 3.0±1.4 h. Additionally, the transit of the test preparation was monitored by a direct examination of the dog intestine by abdominal incision. In this study, the delivery of these preparations to the ascending colon at 4 hr after administration was confirmed. In addition, to estimate the colon arrival time in the beagle dogs, sulfasalazine which is a pro-drug of 5ASA and is cleaved to sulfapyridine and 5ASA in the colon by azo-reductase of intestinal microflora was administered to the dogs. Sulfapyridine starts to appear in the blood circulation at 4 hr after administration and reaches to its maximum concentration at 10–12 hr (J. Pharm. Pharmacol., 1995 in press). Accordingly, colon arrival time has been estimated to be 4 hr in our beagle dogs.

Figure 12:
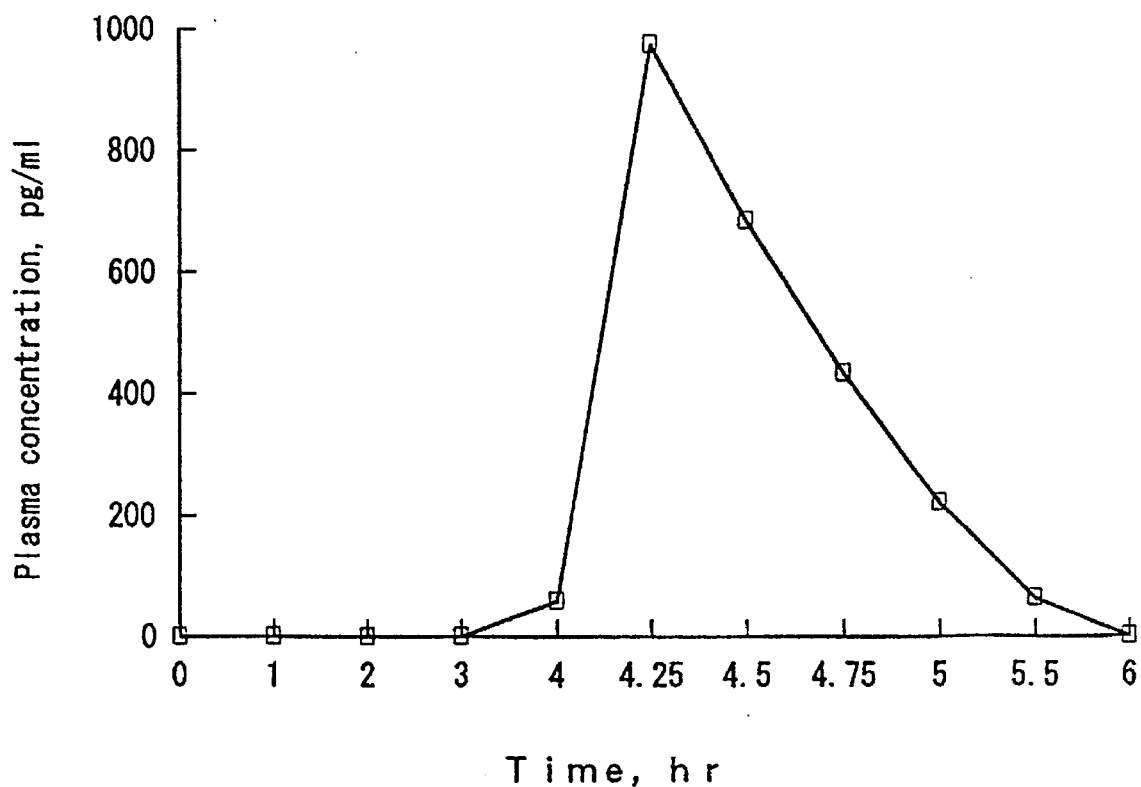
FIG. 12. Plasma calcitonin concentration vs. time curve after oral administration of preparation in Example 7 to male beagle dog.
Figure 13:
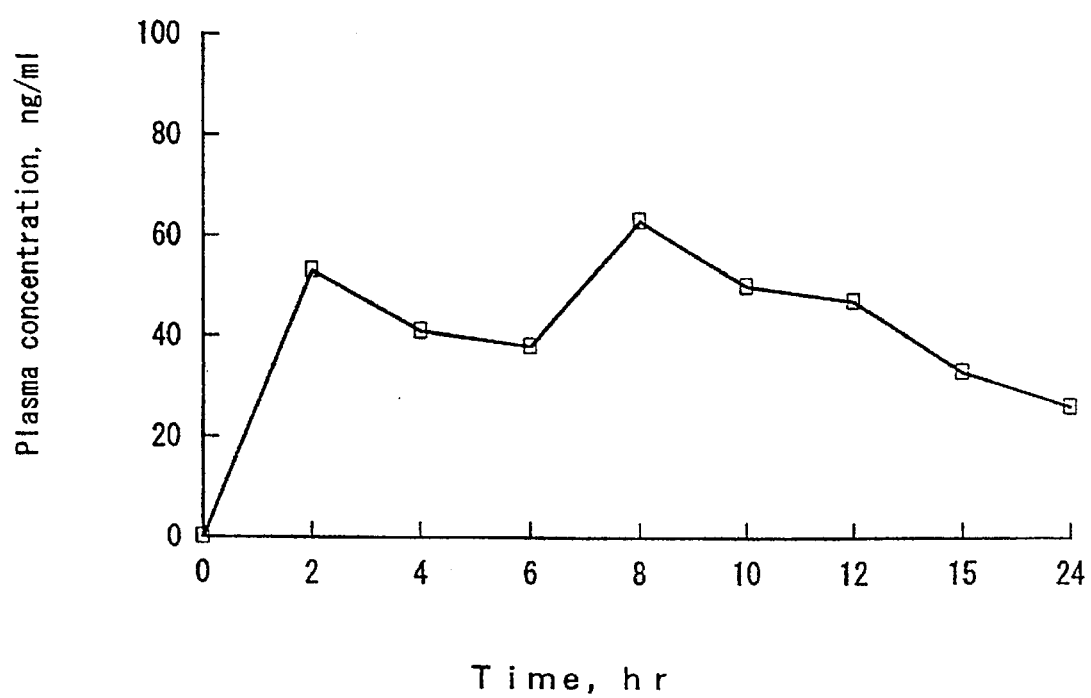
FIG. 13. Plasma diltiazem concentration vs. time curve after oral administration of preparation in Example 8 to male beagle dog.
Figure 14:
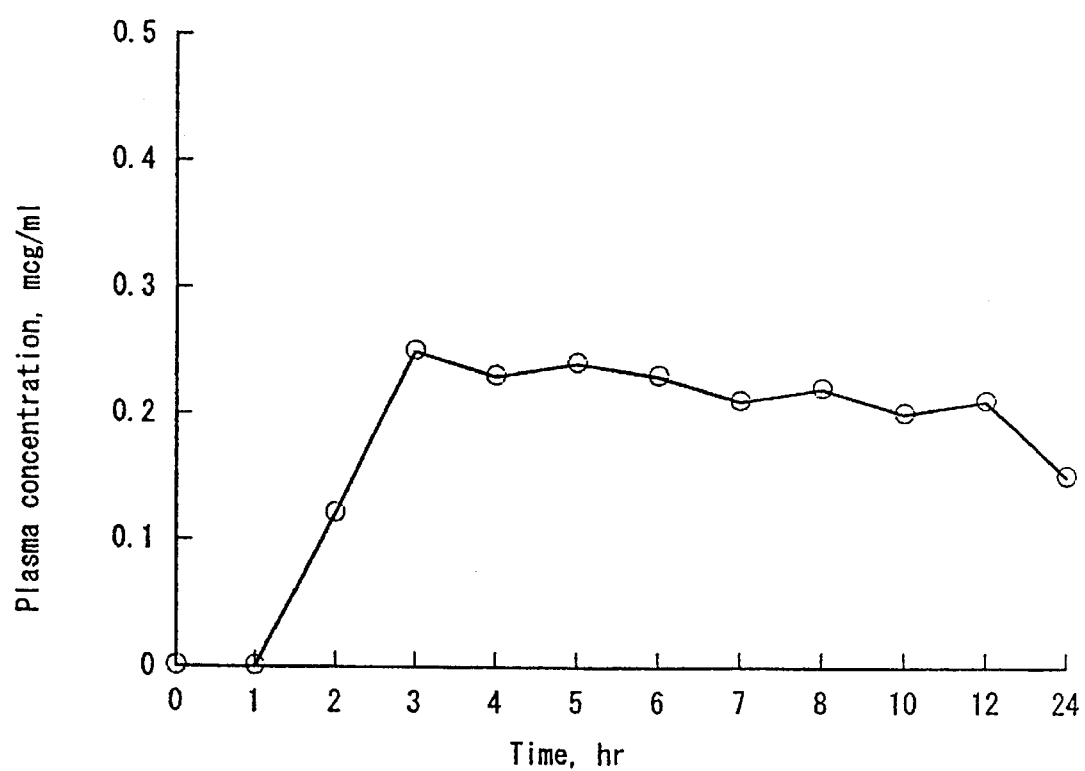
FIG. 14. Serum platinum concentration vs. time curve after oral administration of preparation in Example 9 to male beagle dog.

FIG. 12 shows the plasma calcitonin level vs. time curve of preparation of Example 7. By delivering calcitonin to the colon, the hydrolysis of this peptide drug was thought to be decreased and calcitonin was detected in the blood circulation. FIGS. 13 and 14 show the plasma diltiadem and cisplatin levels vs. time curves for preparations of Example 8 and 9. These results support the sustained-release characteristics of these preparations.

Pharmacodynamic Study of Preparation Containing rhG-CSF

Method

The test capsule, a preparation of Example 6, was orally administered to beagle dogs. At 30 min before drug administration, 0.6 ml of the blank blood sample was removed from the dog jugular vein. After administration, 0.1 ml of blood samples were collected at 10, 24, 36, 48, 60, 72 and 96 h. Fifty ml of the blood sample was used for blood total leukocyte (BTL) count. The BTL count was performed by microcell counter CC-180A (Sysmex, Toa Medical Electronics). The BTL count is expressed as a relative value, which is obtained by the respective control BTL count, namely the pre-dosing BTL count.

Test Result

Figure 15:
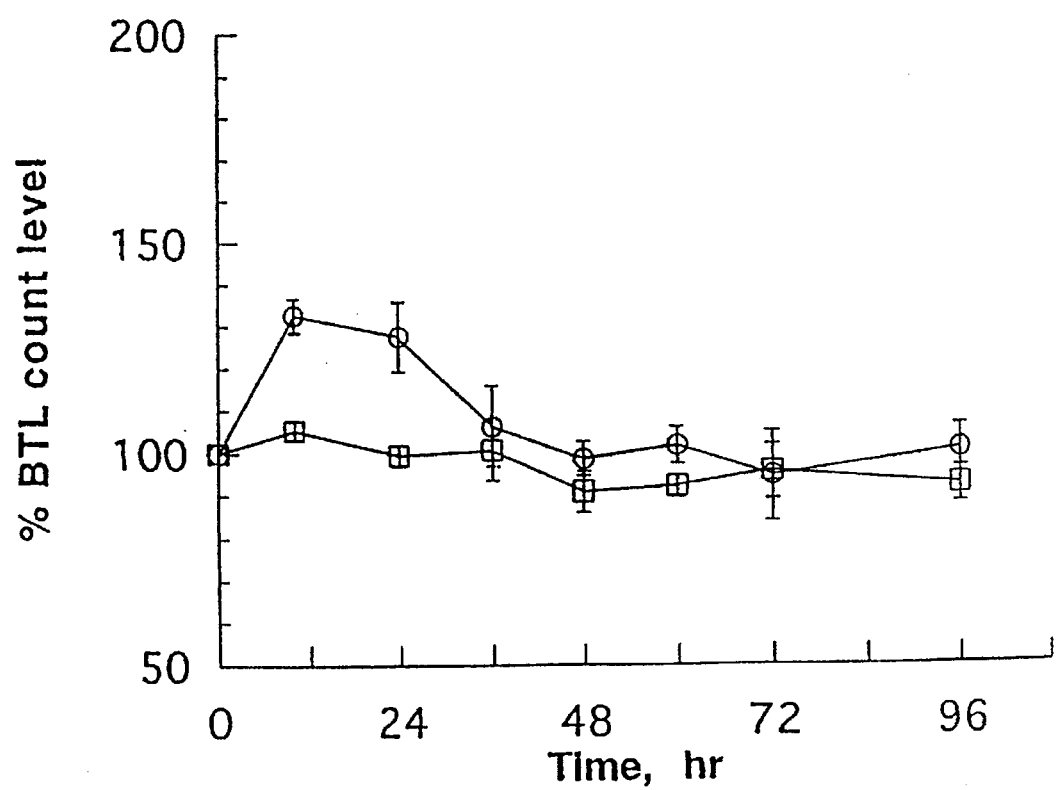
FIG. 15. Time courses of blood total leukocyte count levels after oral administration of preparation in Example 6 to male beagle dogs.

FIG. 15 shows the time course of blood BTL count levels in three dogs after oral administration of rhG-CSF, 25 μg/kg.

BTL count starts to increase at 10 h after administration and reaches 1.3 folds of pre-dose level. Thereafter, BTL count gradually decreases and returns to the normal level at the end of the experiment, 96 h. This result show the efficiency of this innovation for the oral delivery of protein drugs.

Discussion

The mechanism on the disintegration of the time-controlled preparations like Examples 1, 2 and 3 is simply due to the balance between the swelling pressure of the swellable substance and the tolerability of the EC cap. Therefore, both the degree of swelling of the swellable substance and the thickness of the water-insoluble membrane are thought to affect the drug release time from the preparation. As the medium penetrates inside the preparation through micropores, the pore size is thought to affect the in vitro drug release time from the EC capsule. However, when the micropore size was larger than 500 μm, the loss of swellable substance particle occurred. Furthermore, in the case of one micropore made at the bottom of the EC capsule, if the penetration of the medium was disturbed by any unknown factor, the in vitro release experiment would not give us a precise result. Therefore, the number and the size of the micropore made on the capsule body were 4 micropores having 400 μm diameter in the preparation of Example 1.

Figure 16:
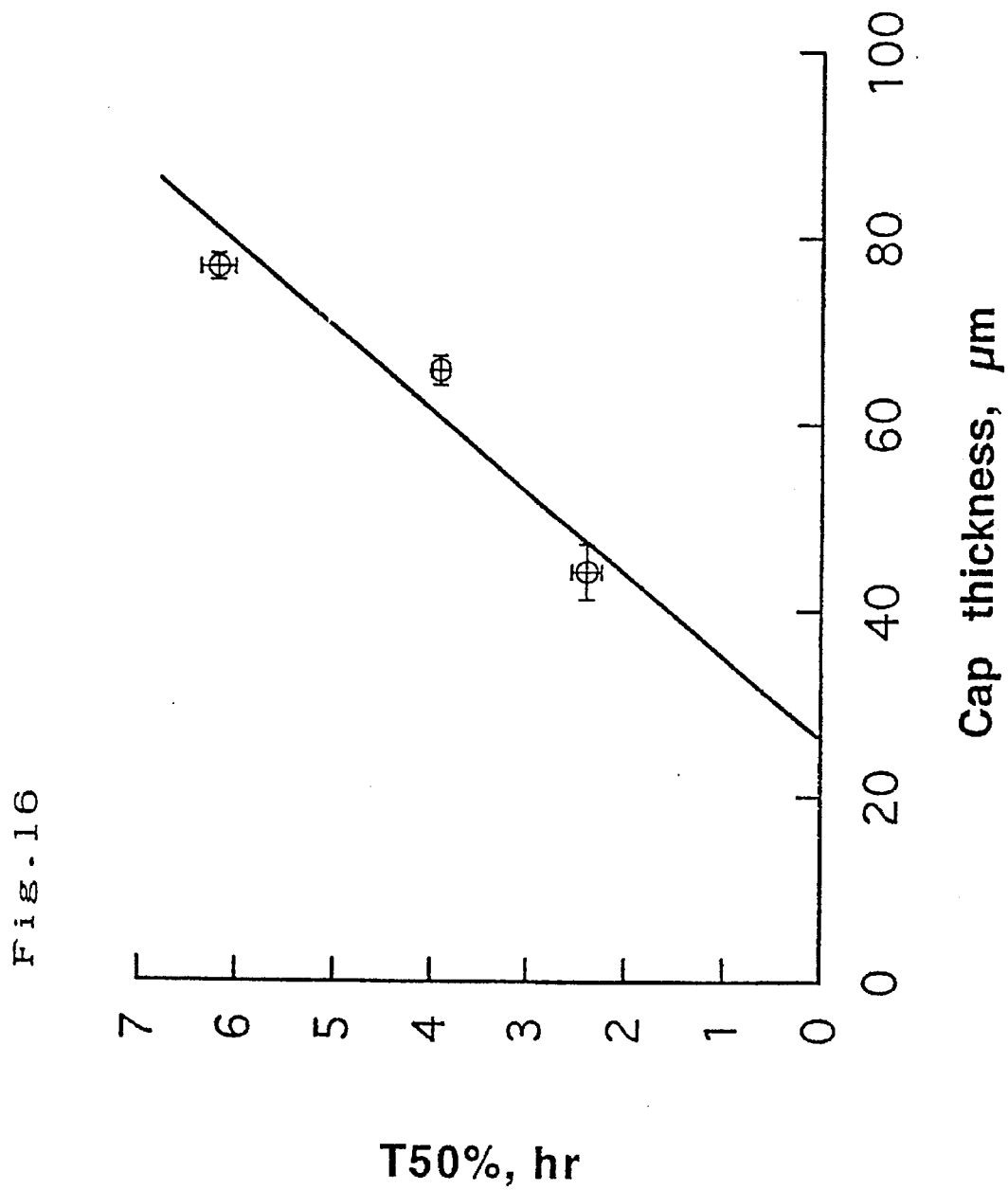
FIG. 16. Relationship between in vitro drug release time and the thickness of EC cap of time controlled-release capsule.
As swellable substance, the combination of 60 mg of L-HPC (LH-2-0) and 60 mg of L-HPC(LH-11) was used. The line was obtained by a linear regression analysis of the data and the correlation coefficient is 0.948. Each point is the mean of three individual determinations and is expressed as the mean±S.E.
Figure 17:
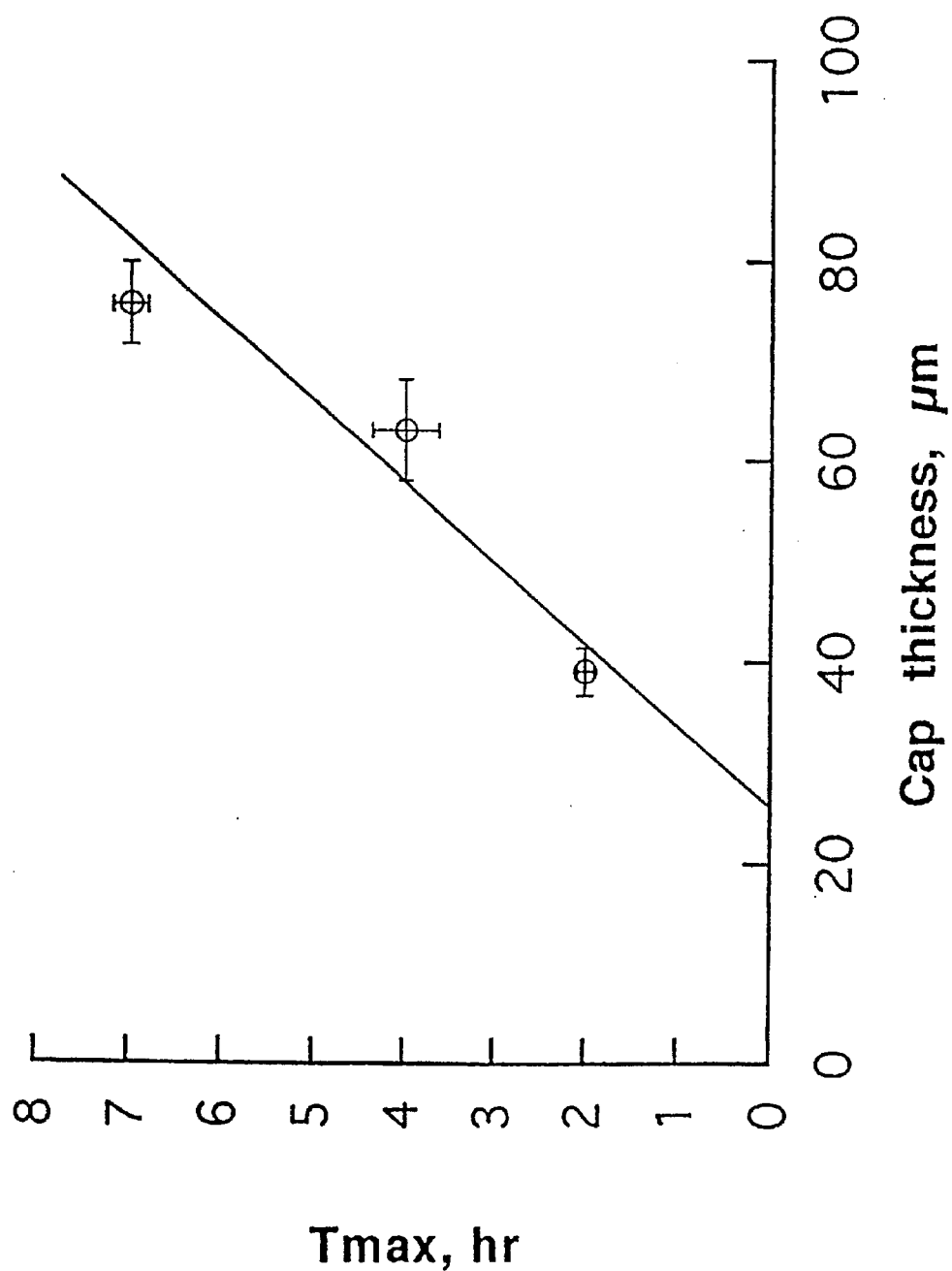
FIG. 17. Relationship between the plasma fluorescein Tmax and the thickness of the cap of time controlled-release capsule. The correlation coefficient is 0.957. Each point is the mean of three individual determinations and is expressed as the mean±S.E.

The innovator has already shown the relationship between the EC cap thickness and the in vitro and in vivo release time in the case of the time controlled-release preparation such as Example 1. (J. Target., 1995, in press). FIG. 16 shows the relationship between the cap thickness and the in vitro T50% when half amount of the drug is released from the time-controlled release capsule though fluorescein was used as a model drug instead of 5ASA. Furthermore, FIG. 17 shows the relationship between the cap thickness and the in vivo Tmax when plasma fluorescein concentration reaches to its maximum level. The test capsules contained the mixture of 30 mg of fluorescein and 220 mg of starch. After the oral administration of capsule to male beagle dogs, plasma fluorescein levels were measured for 10 h. A good relationship was obtained between the Tmax obtained in the in vivo dog study and the thickness of the cap (r=0.957).

Figure 18:
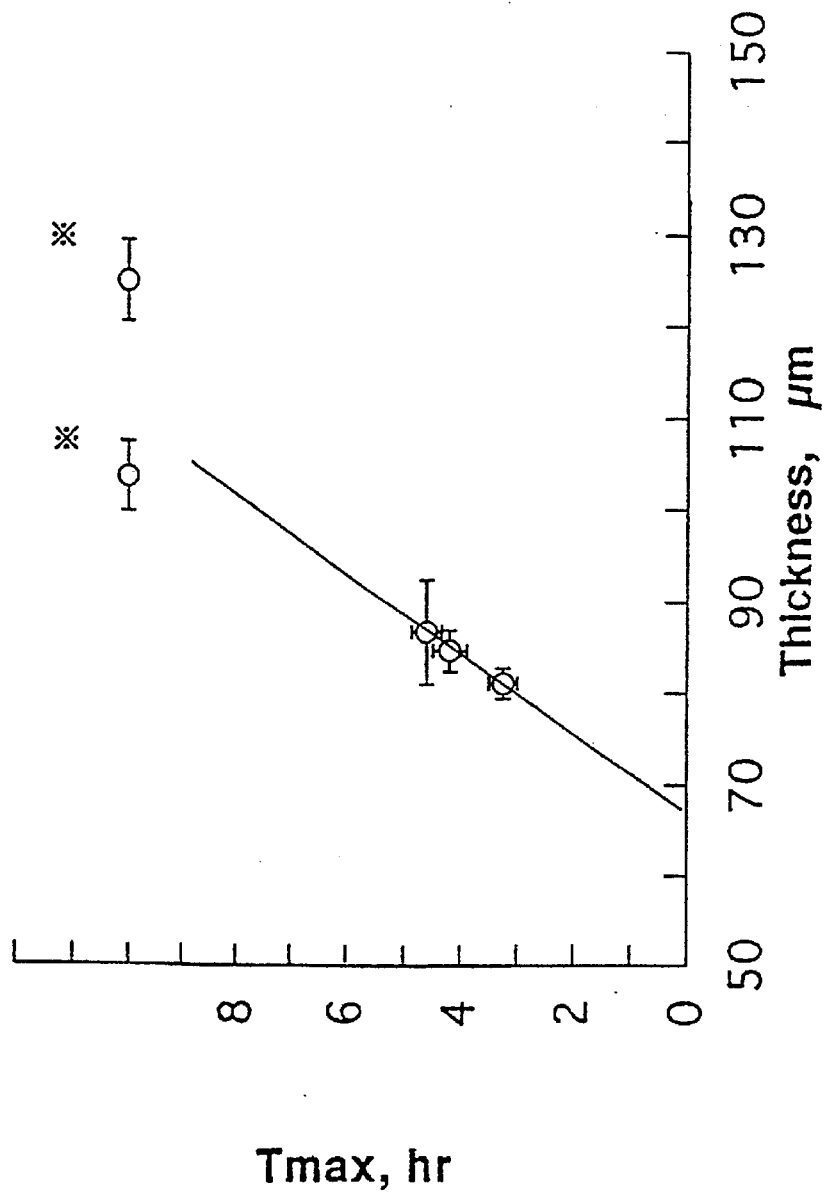
FIG. 18. Relationship between the thickness of EC layer of intestinal pressure controlled-release capsules and plasma fluorescein Tmax after oral administration to beagle dogs.

The inventor has also shown the effect of cap thickness on the in vivo release time of intestinal pressure-controlled system like the preparation of Example 4. The in vivo release time was dependent on the EC capsule thickness (J. Pharm. Pharmacol., 1955, in press). FIG. 18 shows a good corelationship between the capsule thickness and the in vivo Tmax though fluorescein was also used as a model drug.

From these results, it is easily suspected that colon delivery of drugs by our innovation is also possible in human patients by adjusting the thickness of the water-insoluble membrane.

With respect to the micropore capsules for oral long-acting preparation, the difference of the gastrointestinal transit time between experimental animals, in this case, rabbits, and human should be taken into consideration. As the gastrointestinal transit time of rabbits is shorter than human, the release rate of drug from the preparation must be decreased to prepare capsule for human patient. As shown in FIGS. 1a, 1b, 1c and 2a, 2b and 2c, both pore number and the amount of formulated gel-forming substance affect the release rate of drug. Therefore, by controlling these two factors for human patients, oral long-acting preparation for human patients can be prepared with ease.

What is claimed is:

1. An oral intestinal pressure controlled-release preparation for targeting a drug to the gastrointestinal tract characterized in that a drug is contained in a space surrounded by water-insoluble membrane of ethylcellulose in a capsule form, and the thickness of said water-insoluble membrane is controlled within a range of 30 to 70 μm so internal pressure caused by stool and peristalsis disintegrates it to selectively release said drug to a site of colon.

* * * * *